(12) United States Patent
Ishihara

(10) Patent No.: US 9,119,553 B2
(45) Date of Patent: Sep. 1, 2015

(54) FLUORESCENCE ENDOSCOPE DEVICE

(75) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 316 days.

(21) Appl. No.: 13/599,372

(22) Filed: Aug. 30, 2012

(65) Prior Publication Data

US 2012/0323072 A1 Dec. 20, 2012

Related U.S. Application Data

(63) Continuation of application No. PCT/JP2011/055051, filed on Mar. 4, 2011.

(30) Foreign Application Priority Data

Mar. 9, 2010 (JP) ................................. 2010-052010

(51) Int. Cl.
*A61B 1/04* (2006.01)
*A61B 1/06* (2006.01)
(Continued)

(52) U.S. Cl.
CPC ............. *A61B 1/0638* (2013.01); *A61B 1/0005* (2013.01); *A61B 1/00009* (2013.01);
(Continued)

(58) Field of Classification Search
CPC ............... A61B 1/043; A61B 1/00004; A61B 1/00009; A61B 1/05; A61B 1/0005; A61B 5/0059; A61B 5/0071; A61B 5/0082; A61B 5/0086
USPC .......... 600/109, 117, 160, 178, 179, 180, 181
See application file for complete search history.

(56) References Cited

U.S. PATENT DOCUMENTS 7,190,818 B2 * 3/2007 Ellis et al. ...................... 382/128
7,783,098 B2 * 8/2010 Douglass et al. ............. 382/128
(Continued)

FOREIGN PATENT DOCUMENTS

CN 1367455 A 9/2002
EP 2 095 758 A1 9/2009
(Continued)

OTHER PUBLICATIONS

European Search Report dated Jan. 2, 2013 from corresponding European Patent Application No. 11 75 3278.8.
(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

Provided is a fluorescence endoscope device including a light source that irradiates with excitation light and white light; an image generator that acquires a fluorescence image by capturing fluorescence generated in a subject irradiated with the excitation light and that acquires a white-light image by capturing return light from the subject irradiated with the white light; an image corrector that corrects the fluorescence image by using the white-light image so as to generate a corrected fluorescence image; a threshold-value setting unit that sets a threshold value on the basis of an average value of gradation values of pixels in the corrected fluorescence image; an image adjuster that increases the contrast in the corrected fluorescence image between an area having gradation values larger than the threshold value, and an area having gradation values smaller than the threshold value; and a monitor that displays the corrected fluorescence image whose contrast is increased.

17 Claims, 16 Drawing Sheets

(51) Int. Cl.
*A61B 1/00* (2006.01)
*A61B 5/00* (2006.01)
*G06T 5/00* (2006.01)
*G06T 5/50* (2006.01)

(52) U.S. Cl.
CPC .............. *A61B1/043* (2013.01); *A61B 1/0646* (2013.01); *A61B 5/0071* (2013.01); *G06T 5/009* (2013.01); *G06T 5/50* (2013.01); *A61B 5/0084* (2013.01)

(56) References Cited

U.S. PATENT DOCUMENTS

| | | | |
|---|---|---|---|
| 2002/0105505 A1* | 8/2002 | Sendai | 345/204 |
| 2002/0161282 A1* | 10/2002 | Fulghum | 600/160 |
| 2002/0168096 A1 | 11/2002 | Hakamata et al. | |
| 2003/0001104 A1 | 1/2003 | Sendai et al. | |
| 2004/0064016 A1* | 4/2004 | Kobayashi et al. | 600/109 |
| 2008/0255460 A1* | 10/2008 | Voegele et al. | 600/476 |
| 2009/0216085 A1 | 8/2009 | Yamazaki | |
| 2010/0016669 A1* | 1/2010 | Takaoka et al. | 600/160 |
| 2010/0059690 A1 | 3/2010 | Ishihara | |
| 2011/0213252 A1 | 9/2011 | Fulghum | |

FOREIGN PATENT DOCUMENTS

| | | |
|---|---|---|
| EP | 2 105 082 A1 | 9/2009 |
| EP | 2 123 213 A2 | 11/2009 |
| JP | 62-247232 | 10/1987 |
| JP | 2002-172082 | 6/2002 |
| JP | 2003-79568 | 3/2003 |
| JP | 2006-43196 | 2/2006 |
| JP | 2006-175052 | 7/2006 |
| JP | 2007-20775 | 2/2007 |
| JP | 2009-279171 | 12/2009 |
| JP | 2009-279172 | 12/2009 |
| WO | WO 00/42910 A1 | 7/2000 |

OTHER PUBLICATIONS

International Search Report dated Apr. 19, 2011 issued in PCT/JP2011/055051.

* cited by examiner

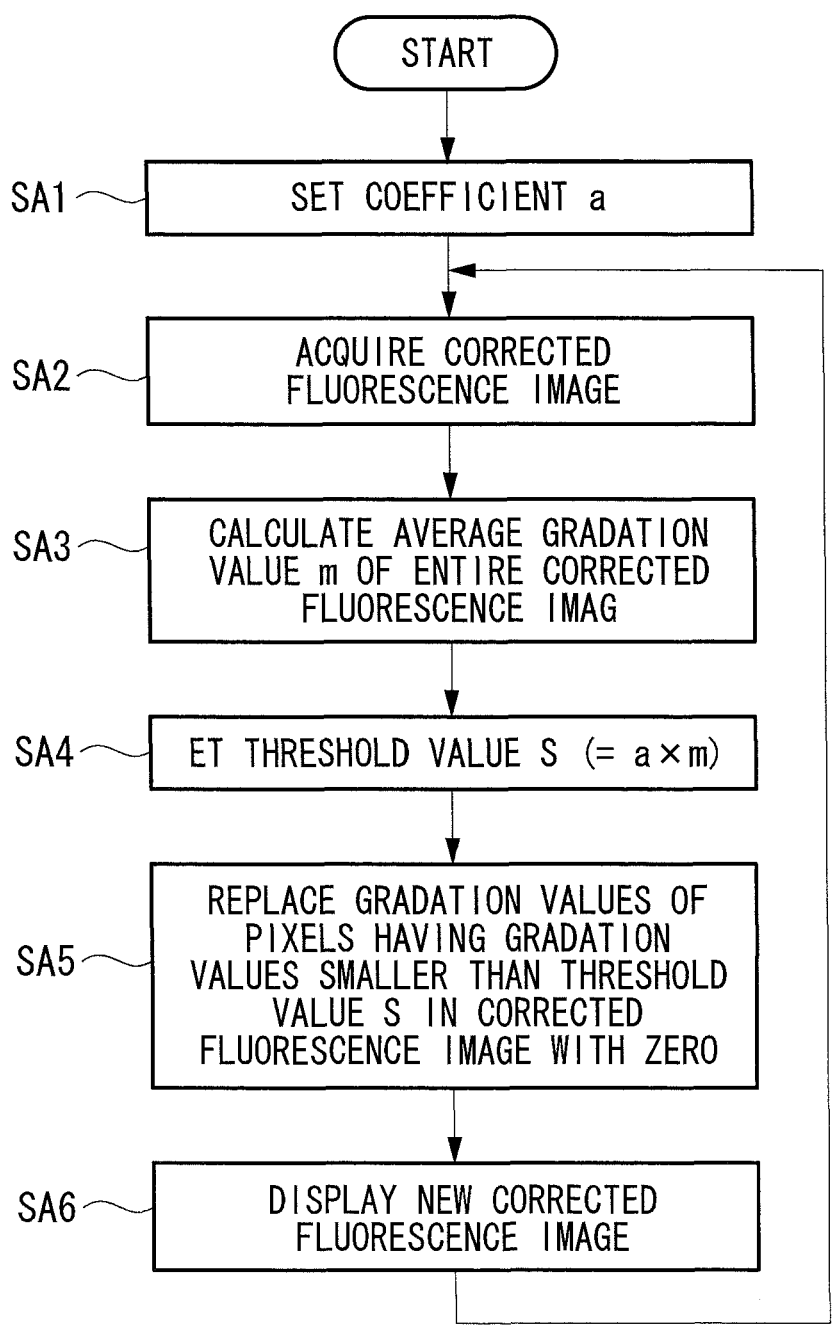

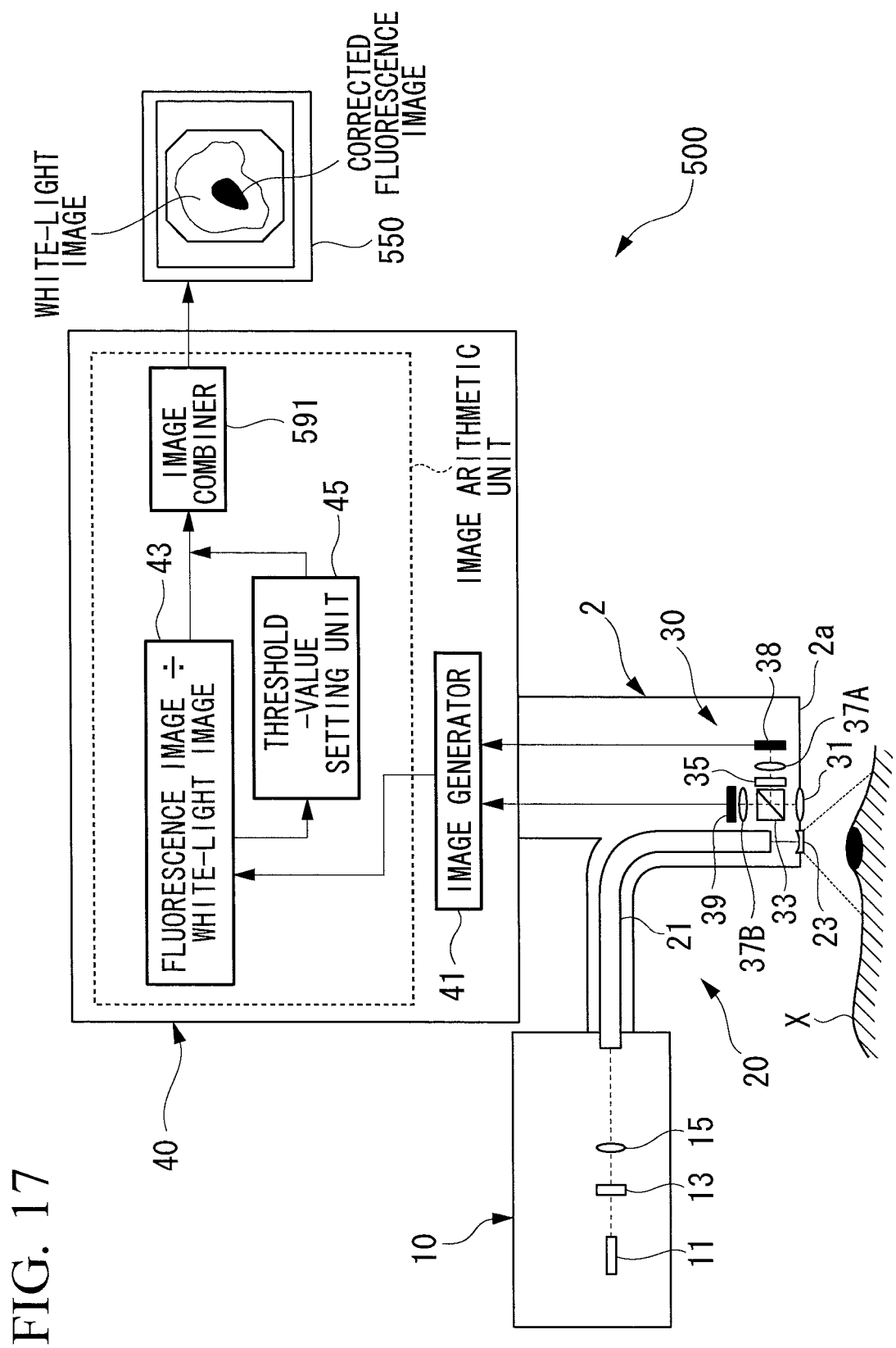

FLUORESCENCE ENDOSCOPE DEVICE

CROSS-REFERENCE TO RELATED APPLICATIONS

This is a continuation of International Application PCT/JP2011/055051, with an international filing date of Mar. 4, 2011, which is hereby incorporated by reference herein in its entirety. This application claims the benefit of Japanese Patent Application No. 2010-052010, the contents of which are incorporated herein by reference.

TECHNICAL FIELD

The present invention relates to fluorescence endoscope devices.

BACKGROUND ART

A known fluorescence endoscope device in the related art radiates excitation light, which generates fluorescence by exciting a fluorescent agent accumulated specifically in a lesion, such as cancer cells, onto an observation site that is administered the fluorescent agent. The fluorescence endoscope device photographs the generated fluorescence so as to acquire a fluorescence image having high luminance in the lesion (for example, see Patent Literature 1). The fluorescence endoscope device discussed in Patent Literature 1 divides the fluorescence image based on the intensity of the fluorescence generated in the observation site irradiated with the excitation light by a reference image based on the intensity of return light returning from the same observation site irradiated with reference light so as to correct a variation in fluorescence intensity, which is dependent on the observation distance, the observation angle, and the like, in the fluorescence image.

CITATION LIST

Patent Literature

{PTL 1} Japanese Unexamined Patent Application, Publication No. 2006-175052

SUMMARY OF INVENTION

An aspect of the present invention provides a fluorescence endoscope device including a light source that irradiates a subject with excitation light and reference light; a fluorescence-image acquisition unit that acquires a fluorescence image by capturing fluorescence generated in the subject irradiated with the excitation light from the light source; a reference-image acquisition unit that acquires a reference image by capturing return light returning from the subject irradiated with the reference light from the light source; a corrected-fluorescence-image generator that corrects the fluorescence image acquired by the fluorescence-image acquisition unit by using the reference image acquired by the reference-image acquisition unit so as to generate a corrected fluorescence image; a threshold-value setting unit that sets a threshold value on the basis of an average value of gradation values of pixels in the corrected fluorescence image generated by the corrected-fluorescence-image generator; an image adjuster that increases a contrast in the corrected fluorescence image between an area having gradation values larger than the threshold value set by the threshold-value setting unit and an area having gradation values smaller than the threshold value; and a display unit that displays the corrected fluorescence image whose contrast is increased by the image adjuster.

When the subject is irradiated with the excitation light emitted from the light source, the fluorescence image of the fluorescence generated in the subject is acquired by the fluorescence-image acquisition unit. When the subject is irradiated with the reference light emitted together with the excitation light from the light source, the reference image of the return light is acquired by the reference-image acquisition unit. Then, the corrected-fluorescence-image generator corrects the fluorescence image by using the reference image with respect to the same object so as to generate a corrected fluorescence image in which a variation in fluorescence intensity that is dependent on the observation distance and the observation angle is reduced.

In the above invention, the corrected-fluorescence-image generator may divide the fluorescence image by the reference image.

Furthermore, in the above invention, the threshold-value setting unit may set a value obtained by multiplying a coefficient by the average value of the gradation values as the threshold value, the coefficient being set such that the coefficient decreases when a percentage at which an area with a predetermined gradation value or higher occupies the corrected fluorescence image increases.

In the above invention, the threshold-value setting unit may set the threshold value on the basis of the average value of the gradation values and a standard deviation.

In this case, the threshold-value setting unit may set a value obtained by adding the standard deviation to the average value of the gradation values as the threshold value.

In the above invention, the threshold-value setting unit may set a value obtained by adding the standard deviation to a value obtained by multiplying a coefficient by the average value of the gradation values as the threshold value, the coefficient being set such that the coefficient decreases when a percentage at which an area with a predetermined gradation value or higher occupies the corrected fluorescence image increases.

In the above invention, the threshold-value setting unit may set a value obtained by adding the average value of the gradation values to a value obtained by multiplying a coefficient by the standard deviation as the threshold value, the coefficient being set such that the coefficient decreases when a percentage at which an area with a predetermined gradation value or higher occupies the corrected fluorescence image increases.

In the above invention, the threshold-value setting unit may set a value obtained by adding a first value to a second value as the threshold value, the first value being obtained by multiplying a first coefficient by the average value of the gradation values, the first coefficient being set such that the first coefficient decreases when a percentage at which an area with a predetermined gradation value or higher occupies the corrected fluorescence image increases, the second value being obtained by multiplying a second coefficient by the standard deviation, the second coefficient being set such that the second coefficient decreases when a percentage at which an area with a predetermined gradation value or higher occupies the corrected fluorescence image increases.

BRIEF DESCRIPTION OF DRAWINGS

FIG. 3 is a flowchart illustrating the operation in the fluorescence endoscope device in FIG. 1.

FIG. 17 schematically illustrates the configuration of a fluorescence endoscope device according to a ninth modification of the embodiment of the present invention.

DESCRIPTION OF EMBODIMENTS

A fluorescence endoscope device according to an embodiment of the present invention will be described below with reference to the drawings.

Figure 1:
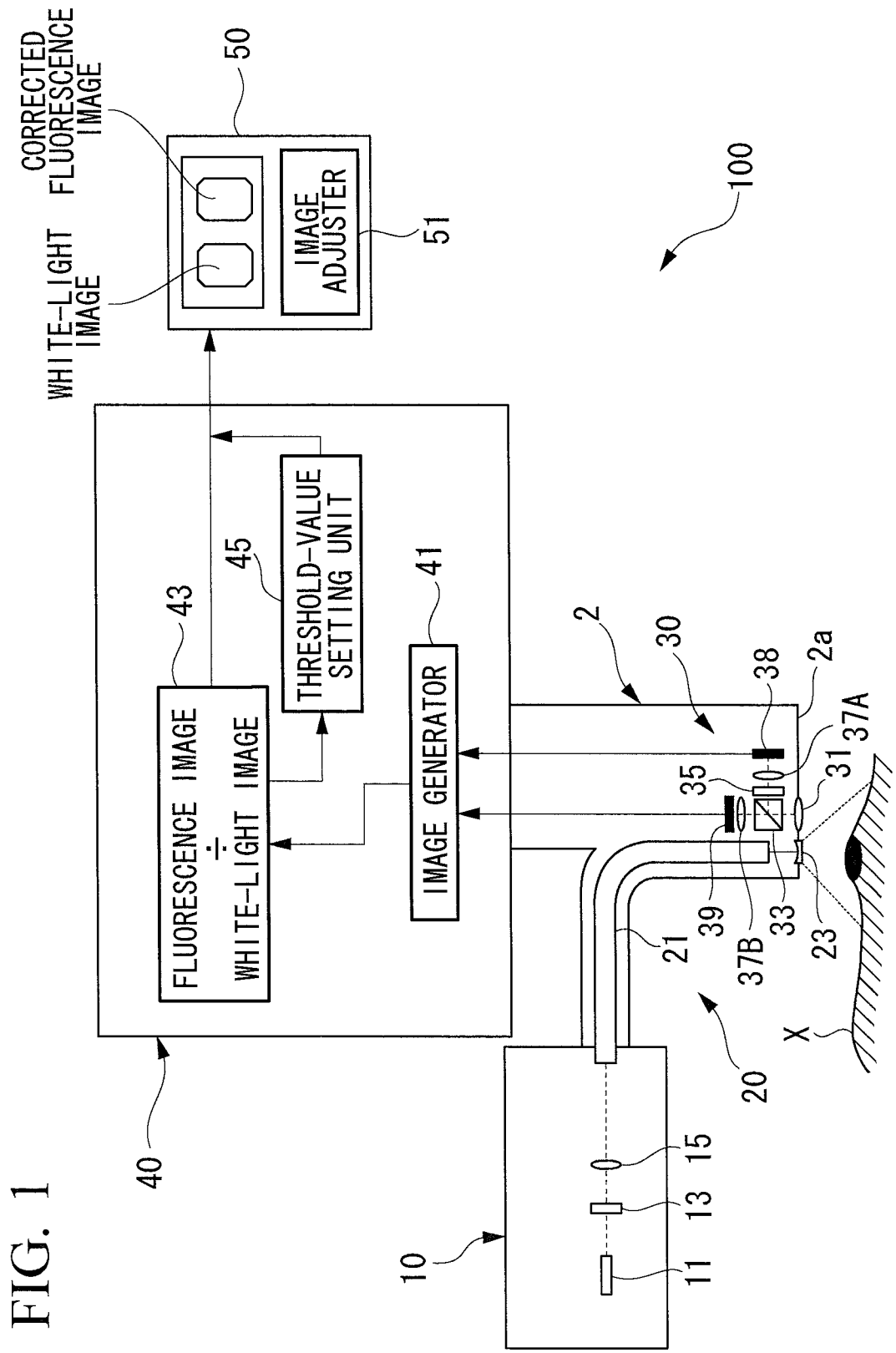
FIG. 1 schematically illustrates the configuration of a fluorescence endoscope device according to an embodiment of the present invention.

As shown in FIG. 1, a fluorescence endoscope device 100 includes a narrow scope 2 to be inserted into a body cavity, an illumination unit 20 having a light source 10 that generates illumination light to be emitted from a tip 2a of the scope 2, an image acquisition unit 30 that is disposed within the scope 2 and acquires image information of an observation site X serving as a subject, an image processor 40 that processes the image information acquired by the image acquisition unit 30, and a monitor (display unit) 50 that displays the image information and an image processed by the image processor 40.

The light source 10 includes a xenon lamp (Xe lamp) 11 that generates the illumination light, an excitation-light filter 13 that transmits white light (reference light) including excitation light from the illumination light generated by the xenon lamp 11, and a coupling lens 15 that focuses the white light including the excitation light transmitted through the excitation-light filter 13. For example, the excitation-light filter 13 transmits white light including excitation light having a wavelength ranging between 400 nm and 740 nm.

The illumination unit 20 includes a light guide fiber 21 extending substantially along the entire length of the scope 2 in the longitudinal direction thereof, and a light spreading lens 23 disposed at the tip 2a of the scope 2.

The light guide fiber 21 guides the white light including the excitation light focused by the coupling lens 15 to the tip 2a of the scope 2. The light spreading lens 23 spreads the white light including the excitation light guided by the light guide fiber 21 so as to irradiate the observation site X with the light.

The image acquisition unit 30 includes an objective lens 31 that collects return light returning from the observation site X irradiated with the white light including the excitation light emitted from the illumination unit 20, and a beam splitter 33 that splits the return light collected by the objective lens 31 in accordance with respective wavelengths.

The objective lens 31 is disposed in parallel with the light spreading lens 23 at the tip 2a of the scope 2. Of the return light, the beam splitter 33 reflects light having an excitation wavelength or longer (i.e., excitation light and fluorescence) and transmits white light having a shorter wavelength than the excitation wavelength (i.e., return light).

The image acquisition unit 30 includes an excitation-light cut filter 35 that only transmits the fluorescence (e.g., near-infrared fluorescence) but blocks the excitation light, which have been reflected by the beam splitter 33, a focusing lens 37A that focuses the fluorescence transmitted through the excitation-light cut filter 35, a focusing lens 37B that focuses the white light transmitted through the beam splitter 33, a fluorescence capturing section 38 that captures the fluorescence focused by the focusing lens 37A, and a white-light capturing section 39 that captures the white light focused by the focusing lens 37B.

For example, the excitation-light cut filter 35 only transmits fluorescence having a wavelength ranging between 765 nm and 850 nm. The fluorescence capturing section 38 is, for example, a high-sensitivity monochrome CCD for fluorescence. The fluorescence capturing section 38 acquires fluorescence-image information by capturing the fluorescence. The white-light capturing section 39 is, for example, a color CCD for white light and includes a mosaic filter (not shown). The white-light capturing section 39 acquires white-light-image information by capturing the white light.

The image processor 40 includes an image generator (fluorescence-image acquisition unit, reference-image acquisition unit) 41 that generates a fluorescence image and a white-light image (i.e., reference image), an image corrector (corrected-fluorescence-image generator) 43 that corrects the fluorescence image generated by the image generator 41 by using the white-light image, and a threshold-value setting unit 45 that sets a threshold value for gradation values in the corrected fluorescence image generated by the image corrector 43.

The image generator 41 generates a two-dimensional fluorescence image from the fluorescence-image information acquired by the fluorescence capturing section 38 and also generates a two-dimensional white-light image from the white-light-image information acquired by the white-light capturing section 39.

The image corrector 43 corrects the fluorescence image by dividing the fluorescence image by the white-light image of the same observation site X. Thus, a corrected fluorescence image with a reduced variation in fluorescence intensity, which is dependent on the observation distance, the observation angle, and the like, in the fluorescence image is generated. Furthermore, the image corrector 43 outputs the white-light image and the generated corrected fluorescence image to the monitor 50.

As shown in the following calculation equation (1), the threshold-value setting unit 45 sets a value obtained by multiplying an average value (i.e., an average gradation value of the entire image) m of the gradation values of the pixels in the corrected fluorescence image by a predetermined coefficient a as a threshold value.

$$S = a \times m \tag{1}$$

The monitor 50 is capable of simultaneously displaying the white-light image and the corrected fluorescence image sent from the image corrector 43. Moreover, the monitor 50 includes an image adjuster 51 that adjusts the gradation values in the corrected fluorescence image.

In order to increase the contrast in the corrected fluorescence image between an area with pixels having gradation values larger than the threshold value S set by the threshold-value setting unit 45 and an area with pixels having gradation values smaller than the threshold value S, the image adjuster 51 displays the pixels having the gradation values smaller than the threshold value S by replacing the gradation values thereof with zero.

The operation of the fluorescence endoscope device 100 according to this embodiment having the above-described configuration will now be described.

In order to observe the observation site X in the body cavity of a living organism by using the fluorescence endoscope device 100 according to this embodiment, a fluorescent agent, which accumulates specifically in a lesion, such as cancer cells, is made to attach to or is absorbed in the observation site X. In this state, the observation site X is irradiated with excitation light so that the fluorescent agent is excited, whereby fluorescence is generated. In actuality, the fluorescent agent not only accumulates in the lesion but also accumulates slightly in normal areas. Thus, weak fluorescence is also generated from areas other than the lesion (i.e., background).

In this embodiment, the scope 2 is first inserted into the body cavity so as to make the tip 2a face the observation site X. In this state, the light source 10 is activated so that the white light including the excitation light generated from the xenon lamp 11 and transmitted by the excitation-light filter 13 is focused by the coupling lens 15 and is guided to the tip 2a of the scope 2 by the light guide fiber 21. Then, the white light is spread by the light spreading lens 23 so as to irradiate the observation site X.

In the observation site X, a fluorescent material contained therein is excited by the excitation light so that fluorescence is generated, and the white light and the excitation light are partially reflected at the surface of the observation site X. The objective lens 31 collects the fluorescence, the white light, and the excitation light, and the beam splitter 33 reflects light having the excitation wavelength or longer, i.e., the excitation light and the fluorescence, and transmits the white light having a shorter wavelength than the excitation wavelength.

With regard to the excitation light and the fluorescence reflected by the beam splitter 33, the excitation light is removed by the excitation-light cut filter 35 so that only the fluorescence is focused by the focusing lens 37A, whereby the fluorescence is captured by the fluorescence capturing section 38. Consequently, the fluorescence-image information of the observation site X is acquired by the fluorescence capturing section 38. The white light transmitted through the beam splitter 33 is focused by the focusing lens 37B so that the white light is captured by the white-light capturing section 39. Consequently, the white-light-image information of the observation site X is acquired by the white-light capturing section 39. The fluorescence-image information and the white-light-image information may be acquired at the same time or may be acquired in any order.

The fluorescence-image information acquired by the fluorescence capturing section 38 and the white-light-image information acquired by the white-light capturing section 39 are input to the image generator 41 in the image processor 40. In the image generator 41, a two-dimensional fluorescence image is generated on the basis of the fluorescence-image information, and a two-dimensional white-light image is generated on the basis of the white-light-image information.

Figure 2A:
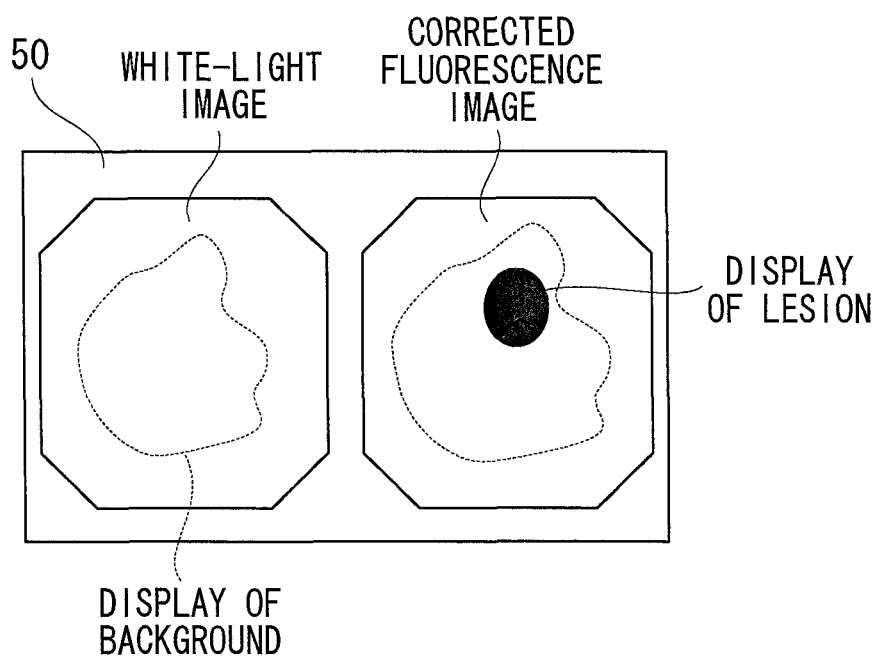
FIG. 2A illustrates an example of a white-light image and a corrected fluorescence image displayed on a monitor in FIG. 1.

The fluorescence image and the white-light image generated by the image generator 41 are sent to the image corrector 43. In the image corrector 43, the fluorescence image is divided by the white-light image so that a corrected fluorescence image is generated. By doing so, a corrected fluorescence image with high quantitative characteristics can be generated by a simple arithmetic process. The generated corrected fluorescence image is sent to the threshold-value setting unit 45 and is also sent to the monitor 50 together with the white-light image so as to be displayed thereon, as shown in FIG. 2A.

Figure 2B:
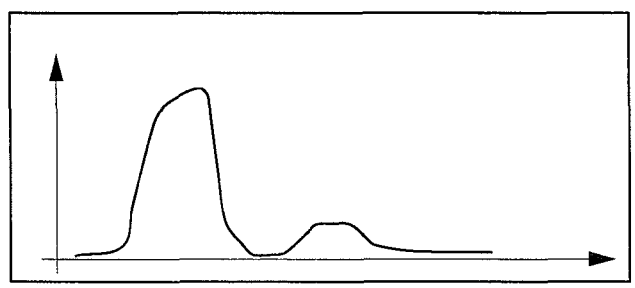
FIG. 2B is a histogram illustrating the relationship between gradation values of pixels in the corrected fluorescence image in FIG. 2A and the frequency of each of the gradation values occupying the entire image.

As shown in FIG. 2B, the corrected fluorescence image is mainly constituted of an area that displays weak fluorescence from the background and an area that displays strong fluorescence from the lesion. In FIG. 2B, the horizontal axis indicates gradation values, whereas the vertical axis indicates the frequency of each of the gradation values occupying the entire corrected fluorescence image (the same applies to FIGS. 4B, 5A, and 6A). A histogram as shown in FIG. 2B may be displayed on the monitor 50.

Because fluorescence and reflected light have different dependencies with respect to the observation distance and the observation angle, there is sometimes a case where a certain error occurs due to not being able to completely compensate for the effects of the observation distance and the observation angle in the corrected fluorescence image.

The following description provided with reference to a flowchart shown in FIG. 3 relates to a threshold-value setting process performed by the threshold-value setting unit 45 and a corrected-fluorescence-image adjustment process performed by the image adjuster 51 for acquiring quantitative information of the observation site X.

In the threshold-value setting unit 45, the coefficient a (e.g., a=1.5) in the aforementioned calculation equation (1) is determined in advance (step SA1). Subsequently, when the threshold-value setting unit 45 acquires a corrected fluorescence image sent from the image corrector 43 (step SA2), the threshold-value setting unit 45 calculates an average gradation value m of the entire image (step SA3).

The average gradation value m of the entire image is calculated from, for example, the following calculation equation (2).

$$m = +(n_1 \times \overline{m_1} + n_2 \times \overline{m_2})/(n_1 + n_2) \qquad (2)$$

where $\overline{m_1}$ denotes an average value of gradation values of pixels displaying the background, $\overline{m_2}$ denotes an average value of gradation values of pixels displaying the lesion, $n_1$ denotes the total number of pixels displaying the background, and $n_2$ denotes the total number of pixels displaying the lesion.

If the corrected fluorescence image has a total of 1,000,000 pixels, it is assumed that 950,000 pixels display the fluorescence from the background (total number of pixels corresponding to the background $n_1=950,000$), and 50,000 pixels display the fluorescence from the lesion (total number of pixels corresponding to the lesion $n_2=50,000$). If the contrast of the fluorescent agent is 1:2, it is assumed that the average gradation value $m_1$ of the background is equal to 1000, and the average gradation value $m_2$ of the lesion is equal to 2000.

Based on this assumption, the average gradation value m (=1050) of the entire image is calculated from calculation equation (2).

Then, the threshold-value setting unit 45 uses the set coefficient a and the calculated average gradation value m of the entire image so as to calculate the threshold value S (=1575) from calculation equation (1). Consequently, the threshold value S for the gradation values in the corrected fluorescence image is set (step SA4) and is sent to the image adjuster 51.

Of all the pixels of the corrected fluorescence image displayed on the monitor 50, the image adjuster 51 replaces the gradation values of pixels having gradation values smaller than the threshold value S (=1575) with zero (step SA5). In this case, assuming that the gradation values of the pixels displaying the background and the gradation values of the pixels displaying the lesion are distributed in accordance with a normal distribution, and the standard deviation is ten times the square root of the average value of the gradation values of the pixels displaying the background and the gradation values of the pixels displaying the lesion, then 96.5% of the display of the background is eliminated, whereas 82.9% of the display of the lesion is maintained.

Figure 4A:
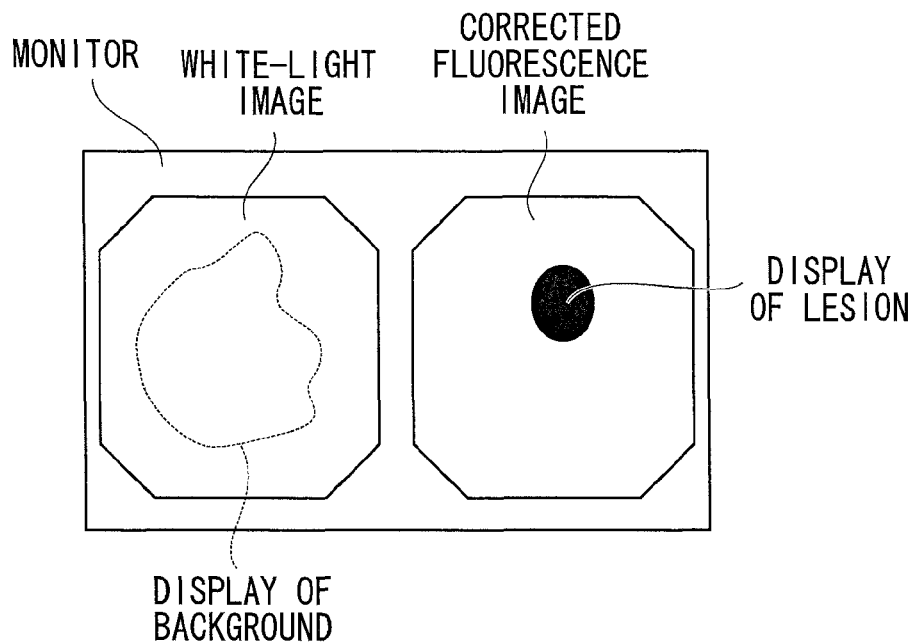
FIG. 4A illustrates an example of the white-light image and a new corrected fluorescence image displayed on the monitor.
Figure 4B:
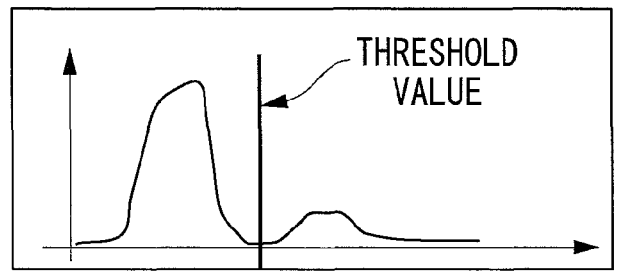
FIG. 4B is a histogram illustrating the relationship between gradation values of pixels in the corrected fluorescence image in FIG. 4A and the frequency of each of the gradation values occupying the entire image.

Consequently, as shown in FIG. 4A, a new corrected fluorescence image with increased contrast between the area displaying the lesion and the area displaying the background is displayed on the monitor 50 (step SA6). As shown in FIG. 4B, the new corrected fluorescence image is mainly constituted of an area that has higher gradation values than the threshold value S and that displays the fluorescence from the lesion.

Figure 5A:
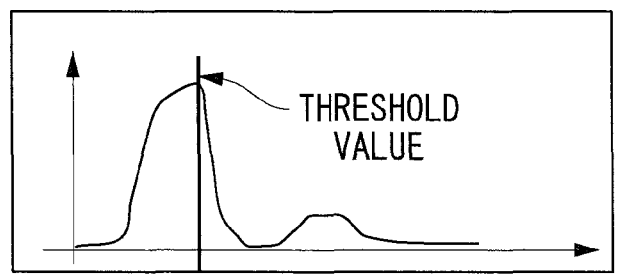
FIG. 5A is a histogram illustrating the relationship between gradation values of pixels in a corrected fluorescence image and the frequency of each of the gradation values occupying the entire image after a change in the gradation values.

Next, it is assumed that the observation distance and the observation angle change, causing the average value of gradation values of pixels in a corrected fluorescence image of a subsequent frame to increase due to an error, as shown in FIG. 5A. In this case, it is assumed that the average value of gradation values of pixels displaying the background and the average value of gradation values of pixels displaying the lesion increase by 50% so as to become $m_1=1500$ and $m_2=3000$, respectively.

Figure 5B:
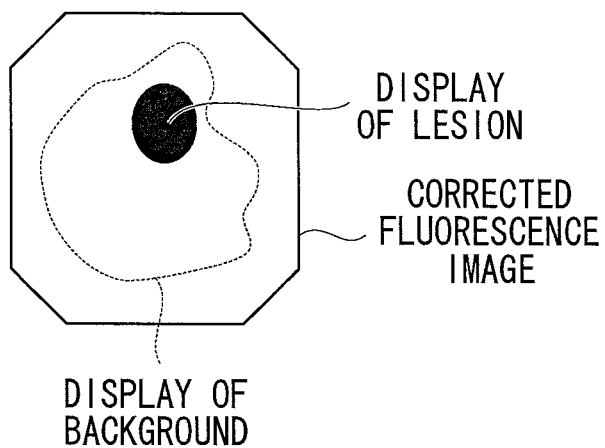
FIG. 5B illustrates an example of the corrected fluorescence image in FIG. 5A.

In this case, assuming that the threshold value S is maintained at 1575 without changing the current threshold value even after the change in the gradation values, an increase in the area having gradation values exceeding the threshold value S causes the display of the background to be eliminated only by 57.7% while 99.5% of the display of the lesion is maintained, as shown in FIG. 5B, resulting in reduced sharpness of the corrected fluorescence image.

In this embodiment, in order for the threshold-value setting unit 45 to set the threshold value S on the basis of the average gradation value m of the entire image, steps SA2 to SA6 are repeated.

Figure 6A:
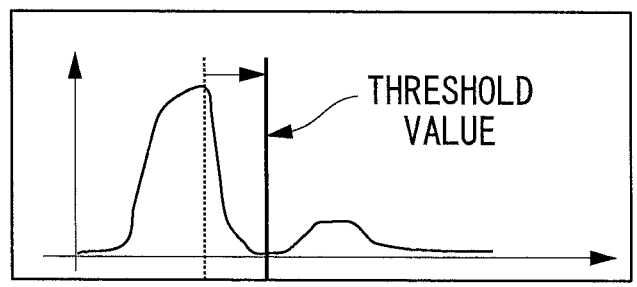
FIG. 6A is a histogram illustrating the relationship between gradation values of pixels in a corrected fluorescence image and the frequency of each of the gradation values occupying the entire image after the image is adjusted.

When the threshold-value setting unit 45 acquires the corrected fluorescence image of the subsequent frame (step SA2), the threshold-value setting unit 45 calculates an average gradation value m of the entire image of the subsequent frame on the basis of calculation equation (2) (step SA3). As shown in FIG. 6A, a new threshold value S (=2363), which is larger than the threshold value S (=1575) for the previous frame, is set (step SA4).

Figure 6B:
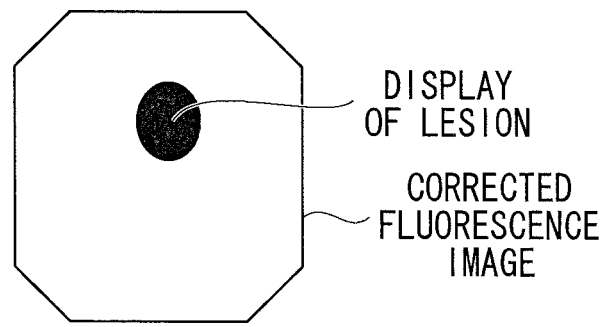
FIG. 6B illustrates an example of the corrected fluorescence image in FIG. 6A.

Consequently, the gradation values in the corrected fluorescence image are adjusted by the image adjuster 51 (step SA5), whereby a new corrected fluorescence image, in which 98.7% of the display of the background is eliminated and 87.8% of the display of the lesion is maintained, is displayed, as shown in FIG. 6B (step SA6).

By repeating steps SA2 to SA6 in this manner, when the corrected fluorescence image of the subsequent frame is generated, the threshold value S is updated on the basis of the average gradation value m of the entire image, whereby a new corrected fluorescence image with adjusted gradation values is displayed on the monitor 50.

As described above, in the fluorescence endoscope device 100 according to this embodiment, the image adjuster 51 adjusts the gradation values of a corrected fluorescence image on the basis of a predetermined threshold value so as to increase the contrast between the lesion and the background, whereby a sharp corrected fluorescence image with reduced effects of weak fluorescence generated from the background can be acquired.

Furthermore, in this embodiment, since a white-light image generated from spread return light and reflected light from a subject is used as a reference image, the gradation values of the reference image are prevented from being zero or values close to zero even in areas that hardly generate fluorescence, whereby an accurate corrected fluorescence image can be generated.

Furthermore, since the threshold-value setting unit 45 sets a threshold value on the basis of an average gradation value of a corrected fluorescence image, the threshold value can be updated in accordance with a change in the gradation values in the corrected fluorescence image, thereby maintaining the degree of sharpness for each acquired corrected fluorescence image. Consequently, quantitative information of the observation site X can be acquired.

Although the coefficient a is set equal to 1.5 as an example in this embodiment, the value of the coefficient a may be changed in accordance with the observation conditions.

This embodiment may be modified as follows.

For example, although the threshold value is set on the basis of the average gradation value m of the entire corrected fluorescence image in this embodiment, the threshold-value setting unit 45 may alternatively set the threshold value S on the basis of the sum of the average gradation value m of the entire image and the standard deviation in a first modification, as shown in the following calculation equation (3)

$$S = m + \sigma \qquad (3)$$

where $\sigma$ denotes the standard deviation of the gradation values of the pixels in the corrected fluorescence image.

Furthermore, although the white-light image is used as a reference image in this embodiment, the white-light image may be acquired by using, for example, a CMOS device or a CCD (white-light-image acquisition unit) formed of three channels, i.e., R, G, and B channels, and the R channel alone, for example, may be used as the reference image.

Alternatively, light in a wavelength range different from that of white light, e.g., infrared or near-infrared light, may be radiated as additional reference light, so as to acquire a reference image different from the white-light image. In either case, since the white-light image and the corrected fluorescence image are simultaneously displayed, additional information about the corrected fluorescence image can be provided to an operator without hindering the observation of the white-light image.

The standard deviation $\sigma$ of the entire image may be calculated from the following calculation equation (4).

$$\sigma^2 = \overline{x^2} - m^2 = (n_1 \times \overline{x_1^2} + n_2 \times \overline{x_2^2})/(n_1 + n_2) - m^2 = \qquad (4)$$
$$(n_1(\sigma_1^2 + m_1^2) + n_2(\sigma_2^2 + m_2^2))/(n_1 + n_2) - m^2$$

where $\overline{x^2}$ denotes a square mean value of the gradation values of the entire image, $\overline{x_1^2}$ denotes a square mean value of the gradation values of the background, $\overline{x_2^2}$ denotes a square mean value of the gradation values of the lesion, $\sigma_1$ denotes a standard deviation of the gradation values of the pixels displaying the background, and $\sigma_2$ denotes a standard deviation of the gradation values of the pixels displaying the lesion.

Ideally, the standard deviation $\sigma_1$ of the background and the standard deviation $\sigma_2$ of the lesion are both values close to the square root of the average gradation value. However, they change significantly due to fluctuations in the distribution of radiated light as well as the effects of protrusions and recesses on the surface of the observation site X. Assuming that each of the standard deviations $\sigma_1$ and $\sigma_2$ is ten times the ideal value (i.e., the square root of the average gradation value), the standard deviation $\sigma_1$ of the background is 316, and the standard deviation $\sigma_2$ of the lesion is 447.

Figure 7:
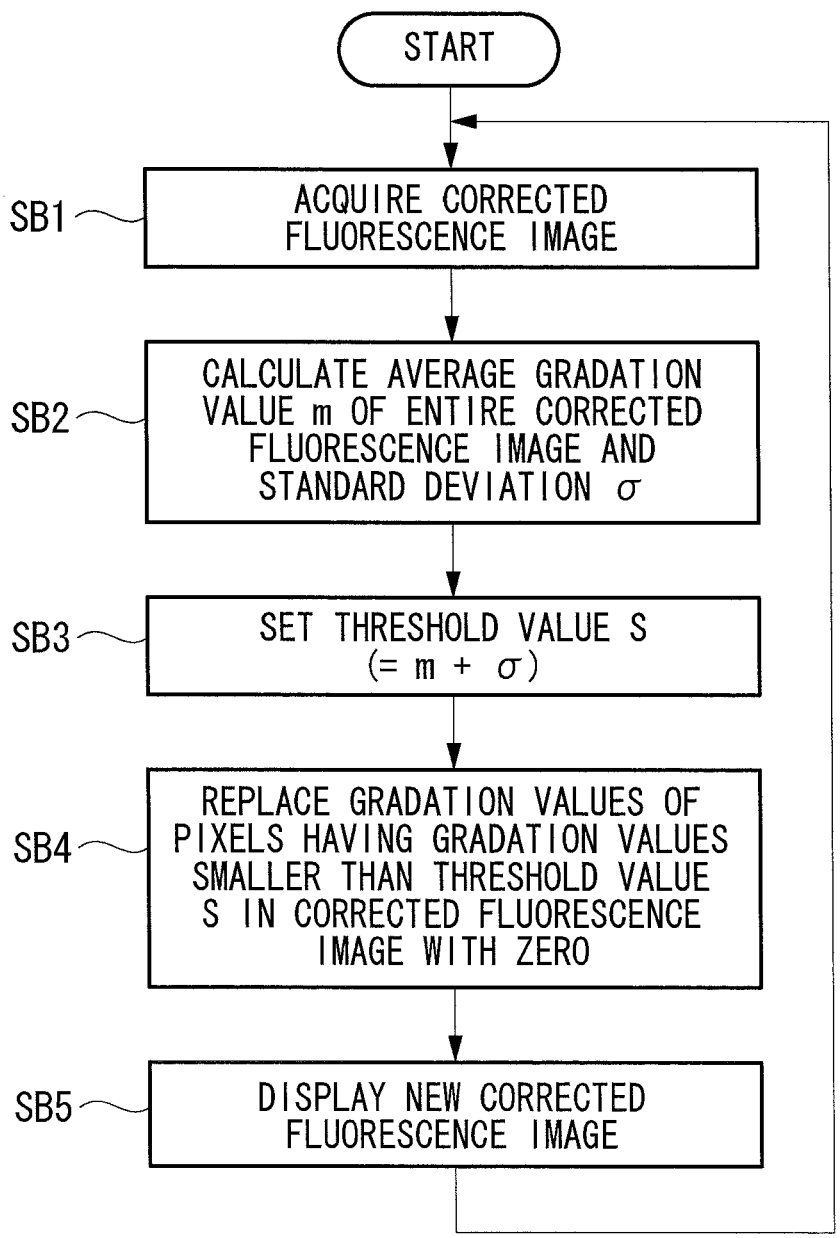
FIG. 7 is a flowchart illustrating the operation of a fluorescence endoscope device according to a first modification of the embodiment of the present invention.

Based on this assumption, referring to a flowchart in FIG. 7, when the threshold-value setting unit 45 acquires a corrected fluorescence image (step SB1), the threshold-value setting unit 45 calculates an average gradation value m (=1050) of the entire image and a standard deviation $\sigma$ (=391) thereof from calculation equations (2) and (4), respectively (step SB2). In the threshold-value setting unit 45, a threshold value S (=1441) is calculated and set based on calculation equation (3) by using the calculated average gradation value m of the entire image and the calculated standard deviation $\sigma$ (step SB3).

Of all the pixels in the corrected fluorescence image, the image adjuster 51 replaces the gradation values of pixels having gradation values smaller than the threshold value S (=1441) with zero (step SB4). Consequently, a new corrected fluorescence image, in which 91.8% of the display of the background is eliminated and 89.5% of the display of the lesion is maintained, is displayed on the monitor 50 (step SB5).

Next, it is assumed that the observation distance and the observation angle change, causing the average value of the gradation values of pixels in a corrected fluorescence image of a subsequent frame to increase due to an error. In this case, assuming that the threshold value S is maintained at 1441 without changing the threshold value, the display of the background is eliminated only by 65.2% while 98.8% of the display of the lesion is maintained after the change in the gradation values, resulting in reduced sharpness of the corrected fluorescence image.

In this modification, in order for the threshold-value setting unit 45 to set the threshold value S on the basis of the sum of the average gradation value m of the entire image and the standard deviation $\sigma$, steps SB1 to SB5 are repeated.

For example, if the average value of the gradation values of the pixels changes by 30%, it is possible to assume that the average gradation value $m_1$ of the background is 1300, the standard deviation $\sigma_1$ thereof is 361, the average gradation value $m_2$ of the lesion is 2600, and the standard deviation $\sigma_2$ thereof is 510.

When the threshold-value setting unit 45 acquires the corrected fluorescence image of the subsequent frame (step SB1), the threshold-value setting unit 45 calculates an average gradation value m (=1365) of the entire image of the subsequent frame and a standard deviation $\sigma$ (=466) on the basis of calculation equations (2) and (4), respectively (step SB2), and sets a new threshold value S (=1831) on the basis of calculation equation (3) (step SB3). Consequently, the gradation values in the corrected fluorescence image are adjusted by the image adjuster 51 (step SB4), whereby a new corrected fluorescence image, in which 92.9% of the display of the background is eliminated and 93.4% of the display of the lesion is maintained, is displayed (step SB5).

With this modification described above, the threshold value S is set on the basis of the sum of the average gradation value m of the entire image and the standard deviation $\sigma$, so that a sharp corrected fluorescence image can always be acquired even if an error remains in the corrected fluorescence image due to the effects of the observation distance and the observation angle. Furthermore, even when the gradation values vary among the pixels in the corrected fluorescence image, a more accurate threshold value can be set, as compared with a case where the threshold value is set on the basis of the average gradation value alone.

A comparative example for this modification will be described below.

For example, if the average value of the gradation values of the pixels changes by 30%, it is assumed that the average gradation value $m_1$ of the background becomes 700, the standard deviation $\sigma_1$ thereof becomes 265, the average gradation value $m_2$ of the lesion becomes 1400, and the standard deviation $\sigma_2$ thereof becomes 374. In this case, if the threshold value S is calculated only on the basis of the average gradation value m of the entire image as a comparative example, the threshold value S is 1103, so that 93% of the display of the background is eliminated while only 78% of the display of the lesion is maintained.

In contrast, when the threshold value S is calculated on the basis of the sum of the average gradation value m of the entire image and the standard deviation $\sigma$, as in this modification, the threshold value S is 1046, so that 90% of the display of the background is eliminated while 83% of the display of the lesion is maintained. Consequently, a threshold value by which the display of the lesion can be maintained at a larger amount can be set, which is advantageous especially when placing higher priority on sensitivity over specificity.

Figure 8:
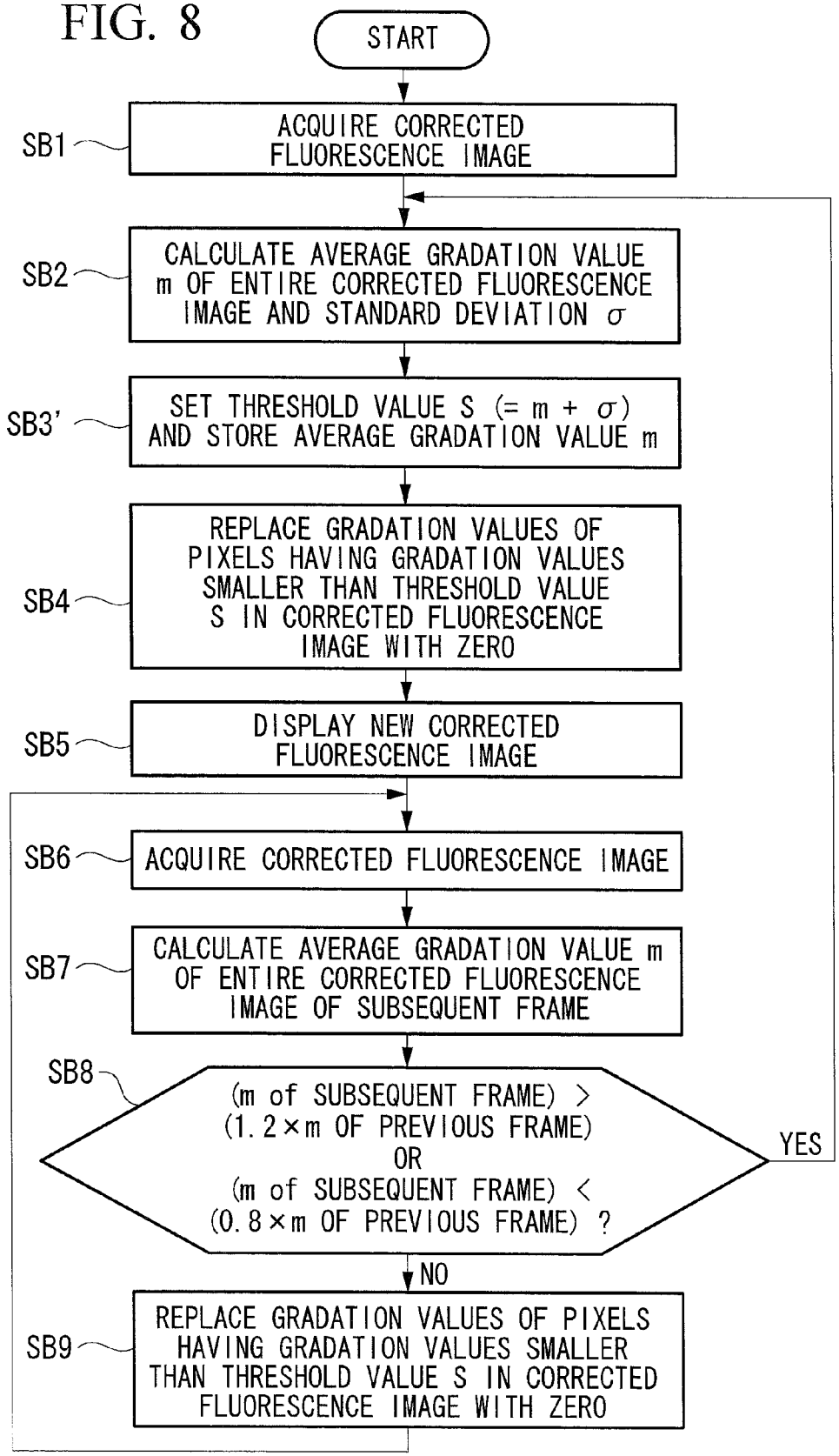
FIG. 8 is a flowchart illustrating the operation of a fluorescence endoscope device according to a second modification of the embodiment of the present invention.

In the above embodiment and this modification, a threshold value S is set for each corrected fluorescence image of a subsequent frame. Alternatively, in a second modification, a threshold value may be set if the average value of the gradation values of the pixels in the subsequent frame changes by more than a specific percentage. In this case, referring to a flowchart in FIG. 8, the threshold-value setting unit 45 sets a threshold value S for the gradation values in a corrected fluorescence image and stores an average gradation value m of the entire image (step SB3'), and performs steps SB4 and SB5 so that a new corrected fluorescence image is displayed.

Subsequently, when the threshold-value setting unit 45 acquires a corrected fluorescence image of a subsequent frame (step SB6), the threshold-value setting unit 45 calculates an average gradation value m of the entire image (step SB7), and compares it with the stored average gradation value m of the entire image of the previous frame (step SB8).

As a result, for example, if the average gradation value m of the entire image of the subsequent frame is greater than or equal to 1.2 times the average gradation value m of the entire image of the previous frame, or smaller than or equal to 0.8 times the average gradation value m of the entire image of the previous frame, steps SB2 to SB8 are repeated. Consequently, a standard deviation σ of the entire image of the subsequent frame is calculated (step SB2), and a new threshold value S is set and a new average gradation value m is stored (step SB3').

On the other hand, in step SB8, if the average gradation value m of the entire image of the subsequent frame is greater than or equal to 0.8 times the average gradation value m of the entire image of the previous frame, or smaller than or equal to 1.2 times the average gradation value m of the entire image of the previous frame, the corrected fluorescence image of the subsequent frame is adjusted without changing the threshold value and is displayed (step SB9). The process then returns to step SB6.

In a state where the observation conditions are relatively stable, the average value of the gradation values of the pixels and the standard deviation do not change significantly. Therefore, a corrected fluorescence image with stable sharpness can be acquired without having to reset the threshold value S every time a corrected fluorescence image is generated. Furthermore, unless the average value of the gradation values of the pixels changes significantly, the threshold value S can be maintained so that the calculation amount of the standard deviation σ can be reduced, thereby achieving improved processing speed.

Figure 9:
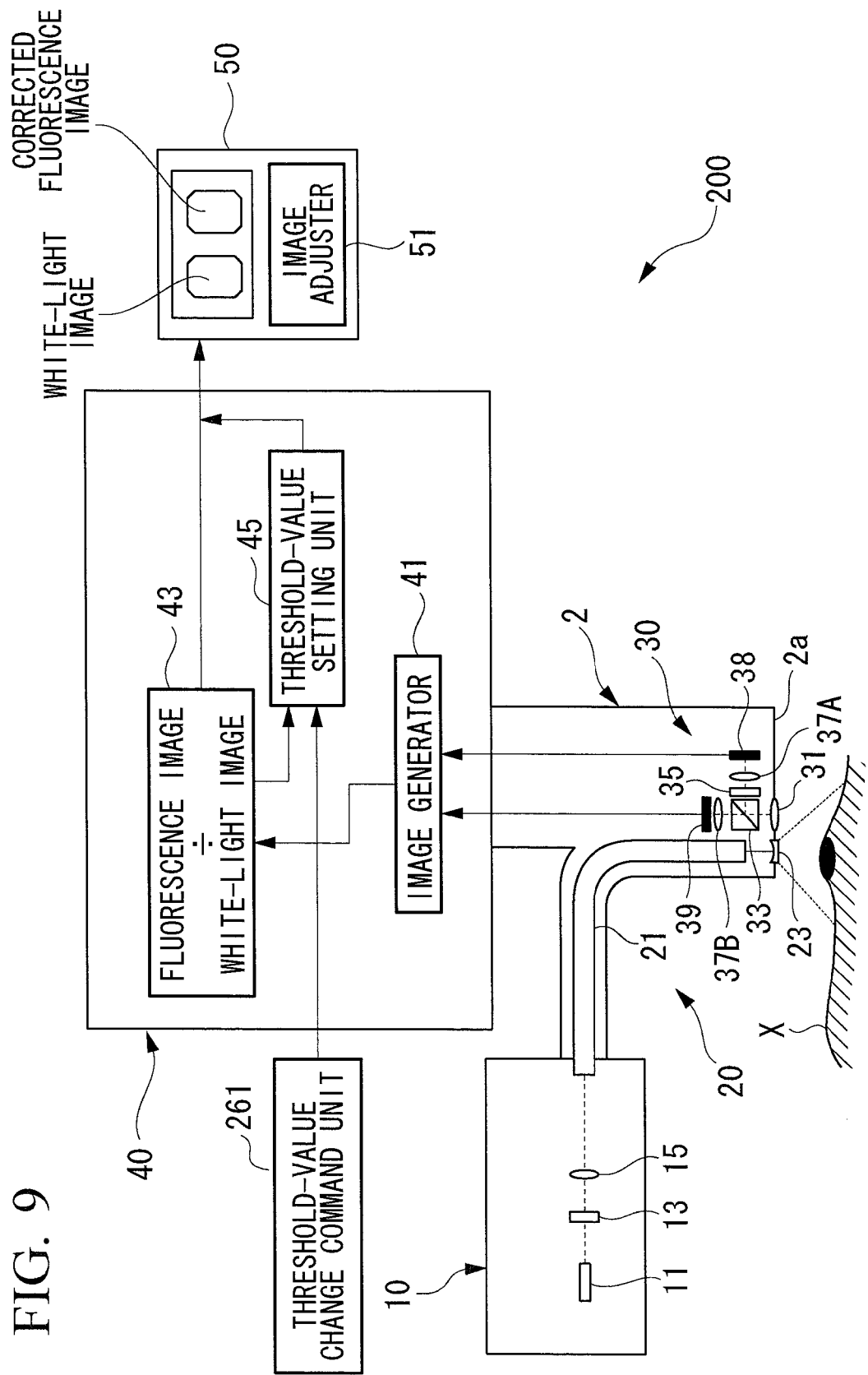
FIG. 9 is a flowchart illustrating the operation of a fluorescence endoscope device according to a third modification of the embodiment of the present invention.

Referring to FIG. 9, in a third modification, a fluorescence endoscope device 200 may include a threshold-value change command unit 261 for inputting a change command for the threshold value, such that an operator may manually change the threshold value by operating the threshold-value change command unit 261. Accordingly, instead of always setting a threshold value every time a corrected fluorescence image of a subsequent frame is generated, the corrected fluorescence image can be adjusted when the operator determines that the threshold value is not appropriate during observation.

Figure 10:
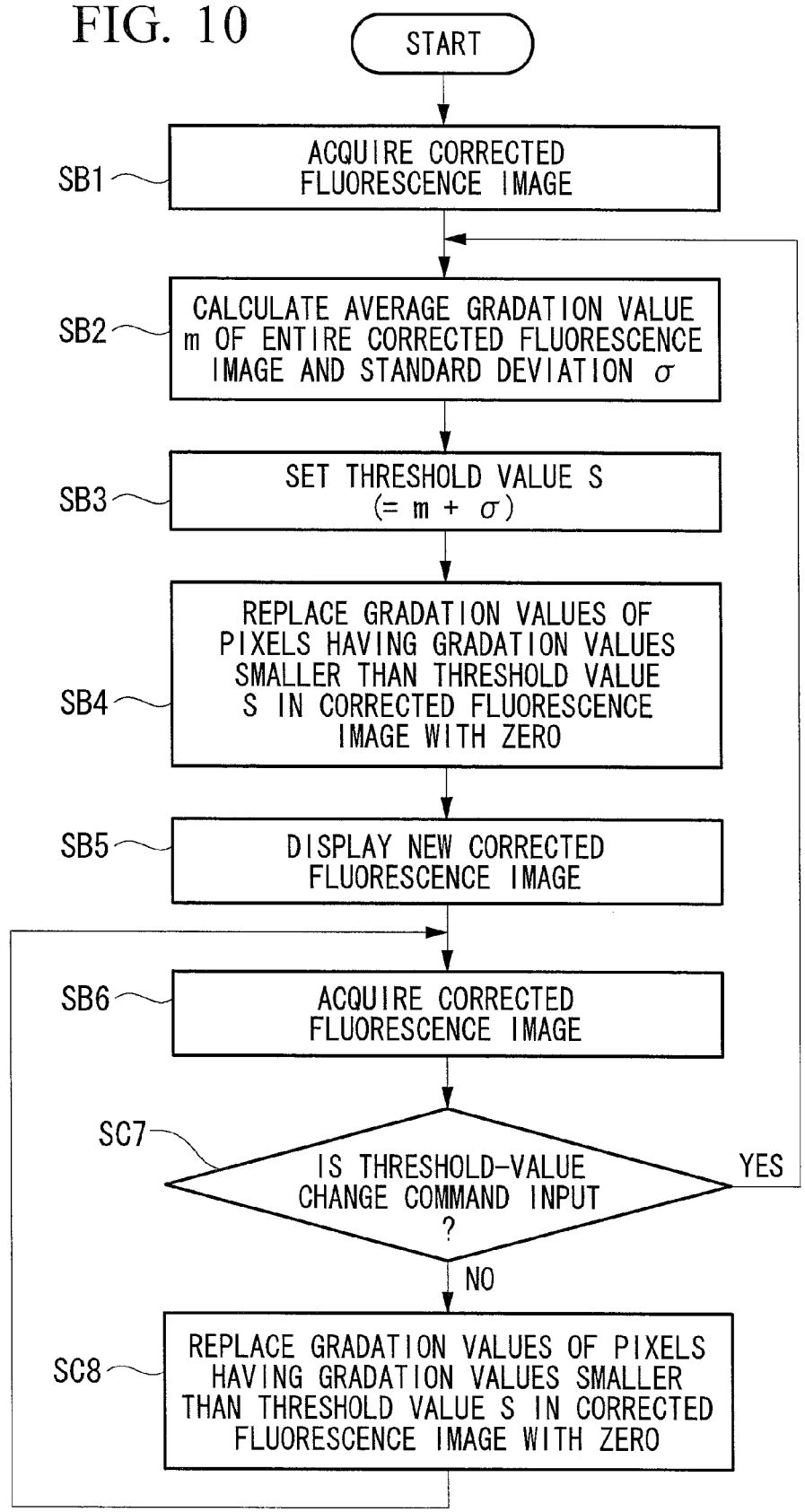
FIG. 10 is a flowchart illustrating the operation of the fluorescence endoscope device in FIG. 9.

In this case, referring to a flowchart in FIG. 10, after a corrected fluorescence image of a subsequent frame is acquired by the threshold-value setting unit 45 (step SB6), if a change command is input to the threshold-value change command unit 261 by the operator ("YES" in step SC7), steps SB2 to SC7 may be repeated. Accordingly, the threshold-value setting unit 45 is activated so that a threshold value S is set on the basis of the sum of the average gradation value m of the entire image of the subsequent frame and the standard deviation σ (step SB3).

On the other hand, if a change command is not input to the threshold-value change command unit 261 by the operator ("NO" in step SC7), the image adjuster 51 may adjust the gradation values of the corrected fluorescence image on the basis of the current threshold value S (step SC8), and the process may return to step SB6.

In a fourth modification, instead of always setting a threshold value every time a corrected fluorescence image of a subsequent frame is generated, a threshold value may be set for every several frames. In this case, for example, information n related to how frequent the threshold value is to be changed may be set in each scope 2, and the fluorescence endoscope device 100 may include a scope-information reader (not shown) that reads the information n from the connected scope 2. Based on the read information n, the threshold-value setting unit 45 may change the threshold value. For example, the information n may indicate that the threshold value should be changed once when a frame number i reaches an n-th frame.

Figure 11:
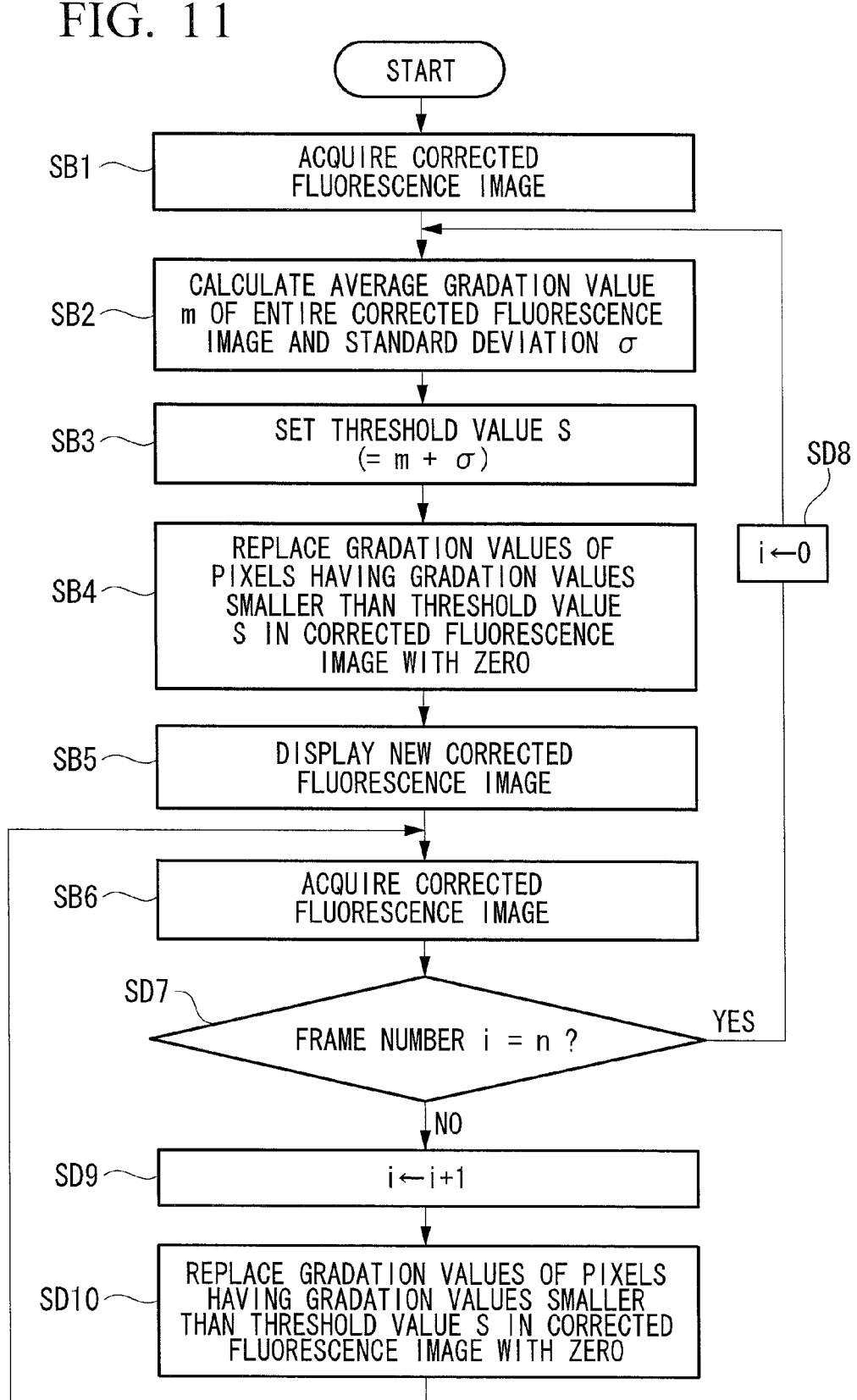
FIG. 11 is a flowchart illustrating the operation of a fluorescence endoscope device according to a fourth modification of the embodiment of the present invention.

In this case, referring to a flowchart in FIG. 11, when the frame number i of a subsequent frame acquired by the threshold-value setting unit 45 in step SB6 reaches the n-th frame ("YES" in step SD7), the frame number i may be reset (step SD8), and steps SB2 to SD7 may be repeated. Accordingly, the threshold value S is set on the basis of the sum of the average gradation value m of the entire image of the subsequent frame and the standard deviation σ (steps SB2 and SB3).

On the other hand, if the frame number i of the subsequent frame has not reached the n-th frame ("NO" in step SD7), a value "1" may be added to the frame number i (step SD9), and the image adjuster 51 may subsequently adjust the gradation values of the corrected fluorescence image on the basis of the current threshold value S (step SD10). The process may then return to step SB6.

Accordingly, the number of times the average gradation value m of the entire image and the standard deviation σ are calculated can be reduced, thereby achieving increased processing speed. For example, under observation conditions in which the observation distance fluctuates significantly due to expansion and contraction thereof, such as inside a stomach, it is better to reset the threshold value S relatively frequently. In contrast, under observation conditions in which the observation distance is relatively fixed, such as inside a large intestine where the lumen diameter is fixed to a certain extent, the threshold value S may be reset less frequently.

In each of the above modifications, the threshold value S is set on the basis of the sum of the average gradation value m of the entire image and the standard deviation σ. Alternatively, for example, in a fifth modification, the threshold-value setting unit 45 may set the threshold value S on the basis of the sum of the average gradation value m of the entire image multiplied by a predetermined coefficient a (i.e., a first coefficient) and the standard deviation σ multiplied by a predetermined coefficient b (i.e., a second coefficient), as shown in the following calculation equation (5).

$$S = a \times m + b \times \sigma \tag{5}$$

The coefficients a and b may be set such that they decrease when an assumed percentage at which the lesion occupies the corrected fluorescence image increases.

Figure 12:
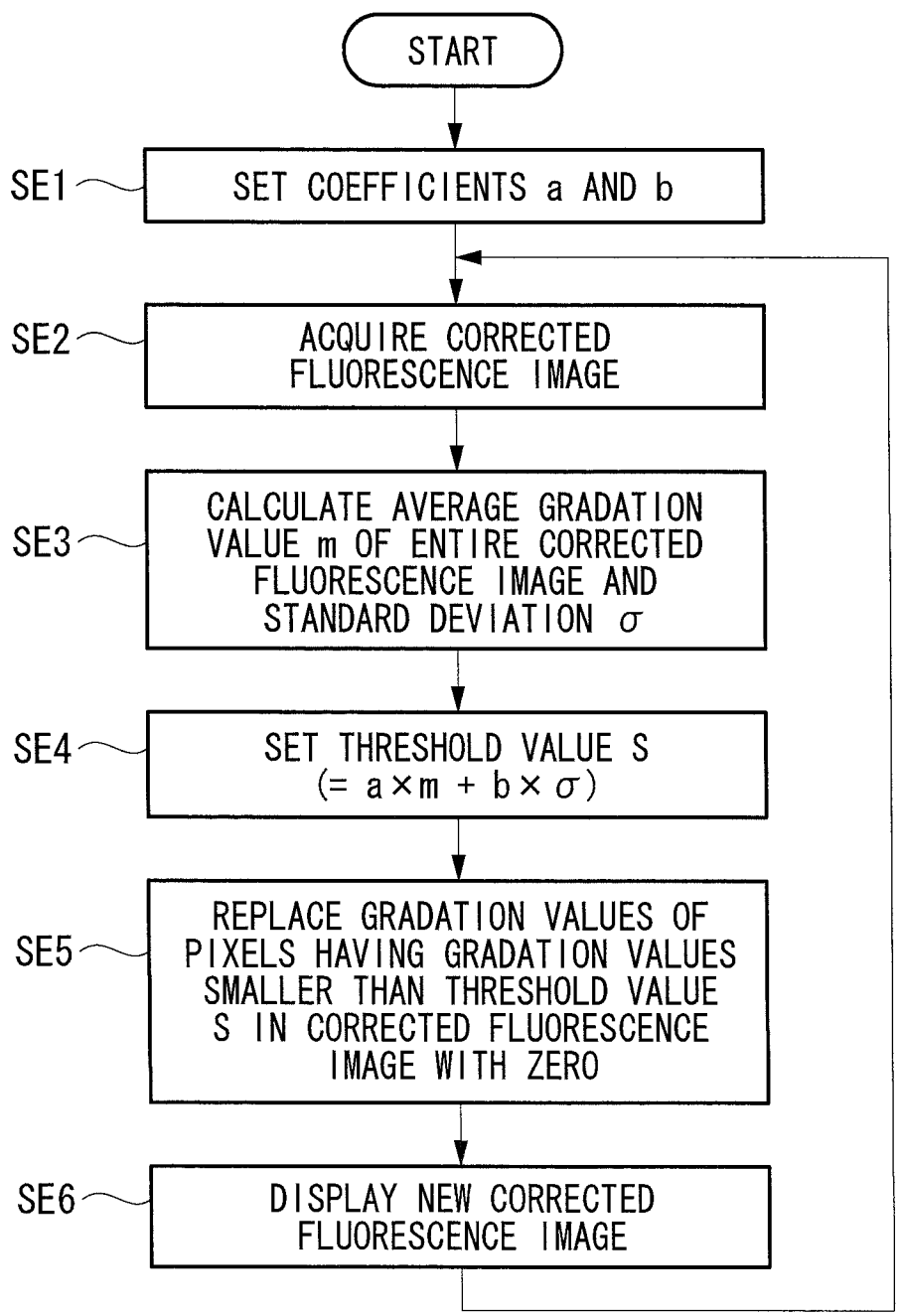
FIG. 12 is a flowchart illustrating the operation of a fluorescence endoscope device according to a fifth modification of the embodiment of the present invention.

In this case, referring to a flowchart in FIG. 12, the threshold-value setting unit 45 first sets the coefficients a and b for the aforementioned calculation equation (5) (step SE1).

The following description relates to an example of how the coefficients a and b are set.

The coefficients a and b are set on the basis of, for example, an assumed average gradation value $m_1$ of the background and an assumed average gradation value $m_2$ of the lesion, and an assumed total number $n_1$ of pixels in the background and an assumed total number $n_2$ of pixels in the lesion, respectively.

It is assumed that the total number of pixels in the corrected fluorescence image is 1,000,000 pixels, the average gradation value $m_1$ of the background is 1000, and the standard deviations $\sigma_1$ and $\sigma_2$ are ten times the ideal values (i.e., the square root of the average gradation values). Then, desired values for the elimination rate for the background and the maintaining rate for the lesion are set in the case where the average gradation value $m_2$ of the lesion is equal to 1500, 2000, 2500, and 3000, as shown in Table 1.

TABLE 1

|  | m2 | | | |
| --- | --- | --- | --- | --- |
|  | 1500 | 2000 | 2500 | 3000 |
| Elimination Rate of Background | 75% | 90% | 95% | 99% |
| Threshold Value S | 1213 | 1405 | 1520 | 1736 |
| Maintaining Rate of Lesion | 77% | 91% | 97% | 99% |

First, a threshold value is set from the elimination rate for the display of the background, and a desired value for the maintaining rate for the display of the lesion at this threshold value is set. In Table 1, the greater the average gradation value $m_2$ of the lesion, the higher the desired values for the elimination rate for the display of the background and the maintaining rate for the display of the lesion.

With this configuration, the threshold value set by the threshold-value setting unit can be prevented from becoming too high even when the standard deviation and the average value of the entire image increase due to an increase in the percentage at which the area with the predetermined gradation value or higher occupies the image, that is, due to an increase in the area occupied by the lesion.

When the coefficient b is equal to 1, the coefficient a can be set on the basis of the relationship between the average gradation value $m_2$ of the lesion and the total number $n_2$ of pixels thereof shown in Table 2. In Table 2, the larger the total number $n_2$ of pixels in the lesion, the smaller the value of the coefficient a.

TABLE 2

|  | m2 | | | |
| --- | --- | --- | --- | --- |
| n2 | 1500 | 2000 | 2500 | 3000 |
| 300000 | 1.06 | 1.08 | 1.05 | 1.08 |
| 250000 | 1.08 | 1.12 | 1.11 | 1.16 |
| 200000 | 1.10 | 1.17 | 1.17 | 1.24 |
| 150000 | 1.13 | 1.22 | 1.24 | 1.34 |
| 100000 | 1.16 | 1.28 | 1.32 | 1.45 |
| 50000 | 1.18 | 1.34 | 1.41 | 1.58 |

For example, when observing a relatively large protruding lesion, like a colon polyp, it can be assumed that the total number of pixels of the lesion would increase since the lesion would occupy a wide region of the corrected fluorescence image. Assuming that the total number $n_1$ of pixels of the background is 700,000 and the total number $n_2$ of pixels of the lesion is 300,000, the coefficients a and b can be set to 0.70 and 1.0, respectively, based on Table 2.

Then, when the threshold-value setting unit 45 acquires a corrected fluorescence image (step SE2), the threshold-value setting unit 45 calculates an average gradation value m (=1300) of the entire image and a standard deviation σ (=583) on the basis of calculation equations (2) and (4), respectively (step SE3). The threshold-value setting unit 45 calculates and sets a threshold value S (=1493) from calculation equation (3) by using the coefficient a (=0.7), the coefficient b (=1), the average gradation value m of the entire image, and the standard deviation σ thereof (step SE4).

The image adjuster 51 adjusts the gradation values of the corrected fluorescence image on the basis of the threshold value S (=1493) (step SE5), whereby a new corrected fluorescence image, in which 94.1% of the display of the background is eliminated and 87.1% of the display of the lesion is maintained, is displayed on the monitor 50 (step SE6).

Accordingly, a minimum value and a maximum value for the threshold value S can be limited on the basis of the percentage at which an area having pixels with high gradation values occupies the corrected fluorescence image. Therefore, the threshold value S is prevented from becoming too high even when the average value of the gradation values increases due to the lesion occupying a wide region of the corrected fluorescence image, whereby the display of the lesion is prevented from being suppressed. On the other hand, the threshold value S is prevented from becoming too low even when the average value of the gradation values decreases due to an area with low gradation values occupying a wide region of the corrected fluorescence image, whereby the display of the background is prevented from being emphasized. In addition, a highly accurate threshold value can be set even when the gradation values vary among the pixels.

As a comparative example for this modification, for example, when the coefficients a and b are set to 1 in a case where the average value of the gradation values increases due to an increase in the percentage at which the lesion occupies the image, the threshold value S is 1883 (=m+σ=1300+583). As a result, the threshold value S is too high, and only 60.3% of the display of the lesion is maintained.

As an alternative to this modification in which the coefficient b is set to 1, the coefficient a may be set to 1 and the coefficient b may be set on the basis of Table 3. Accordingly, a minimum value and a maximum value for the threshold value S can be limited on the basis of the percentage at which an area having pixels with high gradation values occupies the corrected fluorescence image. Therefore, the threshold value S is prevented from becoming too high even when the standard deviation of the gradation values increases due to the lesion occupying a wide region of the corrected fluorescence image, whereby the display of the lesion is prevented from being suppressed. On the other hand, the threshold value S is prevented from becoming too low even when the standard deviation of the gradation values decreases due to an area with low gradation values occupying a wide region of the corrected fluorescence image, whereby the display of the background is prevented from being emphasized.

TABLE 3

|  | m2 | | | |
| --- | --- | --- | --- | --- |
| n2 | 1500 | 2000 | 2500 | 3000 |
| 300000 | 0.70 | 0.63 | 0.51 | 0.46 |
| 250000 | 0.72 | 0.68 | 0.56 | 0.52 |
| 200000 | 0.75 | 0.73 | 0.63 | 0.61 |
| 150000 | 0.78 | 0.79 | 0.72 | 0.72 |
| 100000 | 0.82 | 0.87 | 0.83 | 0.87 |
| 50000 | 0.85 | 0.97 | 0.98 | 1.08 |

When the coefficient b is 0, that is, when the threshold value S is set to equal a×m, the coefficient a may be set on the basis of the relationship between the total number $n_2$ of pixels of the lesion and the average gradation value $m_2$ shown in Table 4.

In this modification, for example, an operator may manually change the threshold value in accordance with the observation conditions by using the threshold-value change command unit 261, as in the fluorescence endoscope device 200 shown in FIG. 9. Accordingly, this is advantageous when lesions with different sizes are found during observation.

TABLE 4

| n2 | m2 | | | |
|---|---|---|---|---|
| | 1500 | 2000 | 2500 | 3000 |
| 300000 | 0.15 | 0.18 | 0.09 | 0.14 |
| 250000 | 0.22 | 0.28 | 0.19 | 0.25 |
| 200000 | 0.29 | 0.39 | 0.31 | 0.38 |
| 150000 | 0.37 | 0.52 | 0.46 | 0.54 |
| 100000 | 0.46 | 0.68 | 0.66 | 0.77 |
| 50000 | 0.56 | 0.91 | 0.96 | 1.16 |

Figure 13:
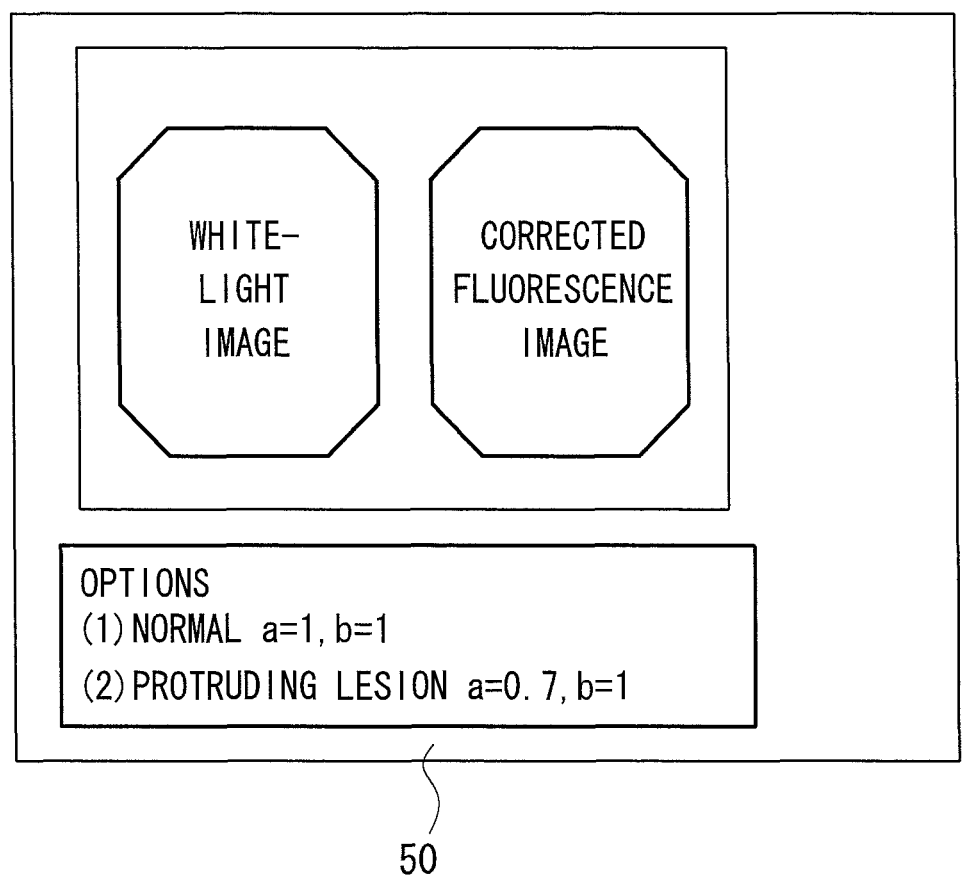
FIG. 13 illustrates an example of options for coefficients a and b displayed on a monitor in a fluorescence endoscope device according to a sixth modification of the embodiment of the present invention.
Figure 14:
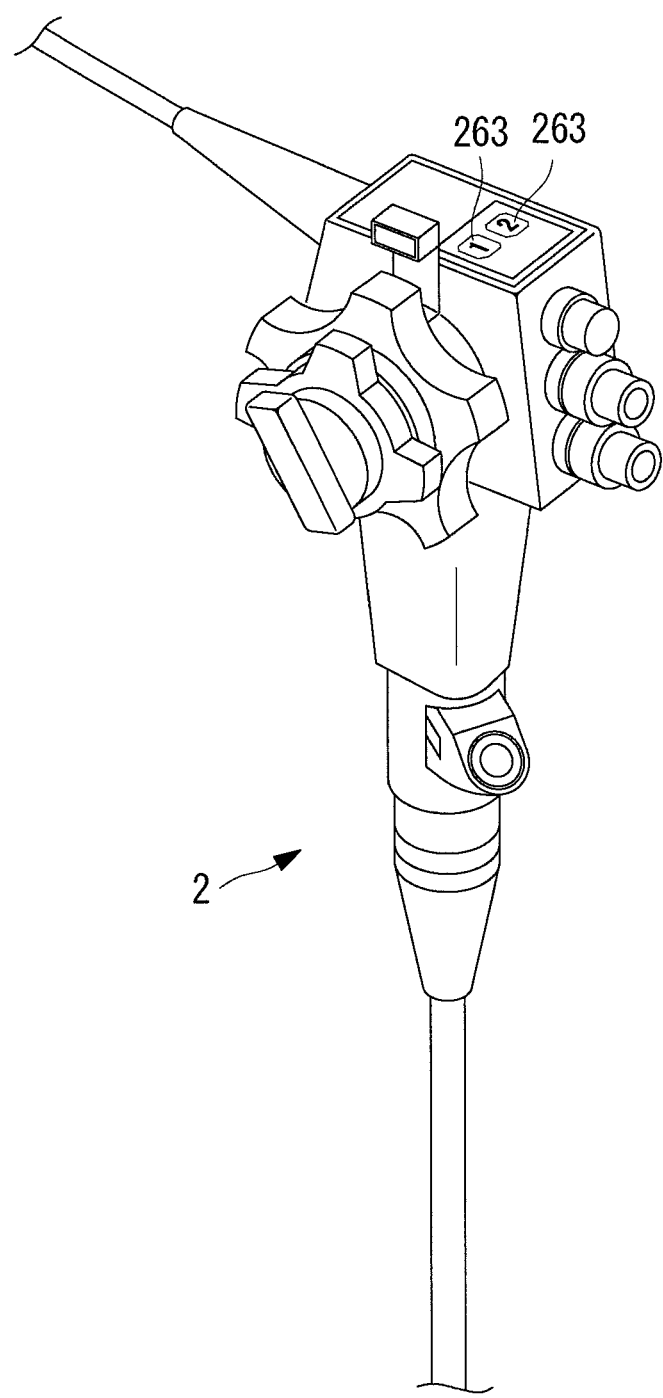
FIG. 14 illustrates a coefficient changing unit provided on a scope.

As an alternative to this modification in which a pair of coefficients a and b is set, for example, multiple pairs of coefficients a and b may be set in a sixth embodiment such that the coefficients a and b may be selected in accordance with the shape of a subject to be observed. In this case, for example, referring to FIG. 13, two pairs of coefficients a and b for when observing a normal lesion having a non-protruding shape and for when observing a protruding lesion may be set and displayed on the monitor 50. Referring to FIG. 14, a coefficient changing unit 263 for changing between these two pairs of coefficients a and b may be provided on the scope 2. The multiple pairs of coefficients a and b may be preset by using Tables 1 to 3 in accordance with the size and the shape of assumed lesions.

Figure 15:
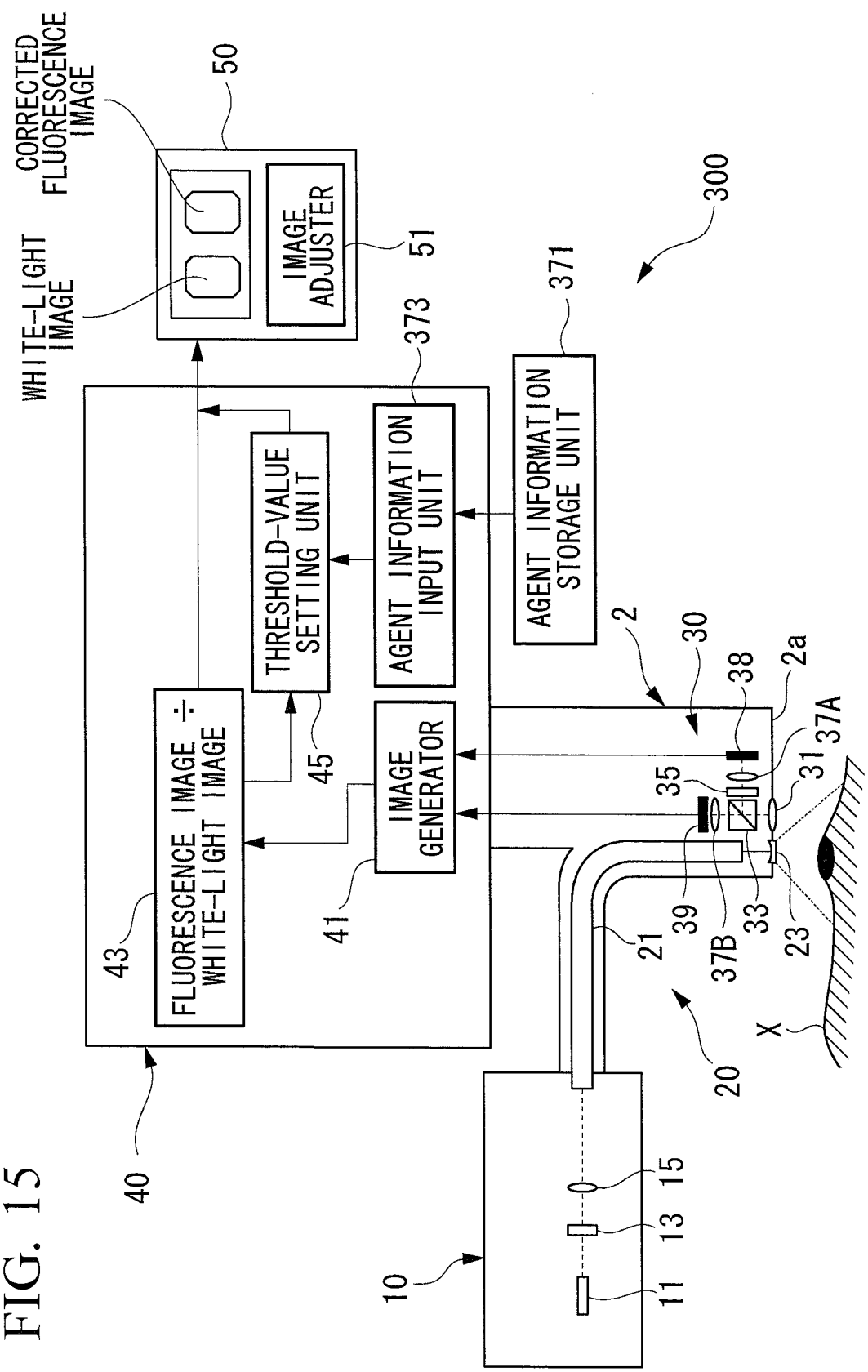
FIG. 15 schematically illustrates the configuration of a fluorescence endoscope device according to a seventh modification of the embodiment of the present invention.

Referring to FIG. 15, in a seventh modification, a fluorescence endoscope device 300 may include an agent information storage unit 371 that stores information about fluorescent agents and information about gradation values corresponding thereto, and an agent information input unit 373 for inputting the information about a fluorescent agent to be used, which is selected by an operator from the agent information storage unit 371, into the threshold-value setting unit 45. Based on the information about the fluorescent agent input to the threshold-value setting unit 45, the coefficients a and b may be selected. When a different fluorescent agent is used, the contrast also changes. Therefore, by making the coefficients a and b selectable in accordance with the types of fluorescent agents, a sharper corrected fluorescence image can be acquired. In this case, the coefficients a and b may similarly be preset by using the aforementioned Tables 1 to 3.

Figure 16:
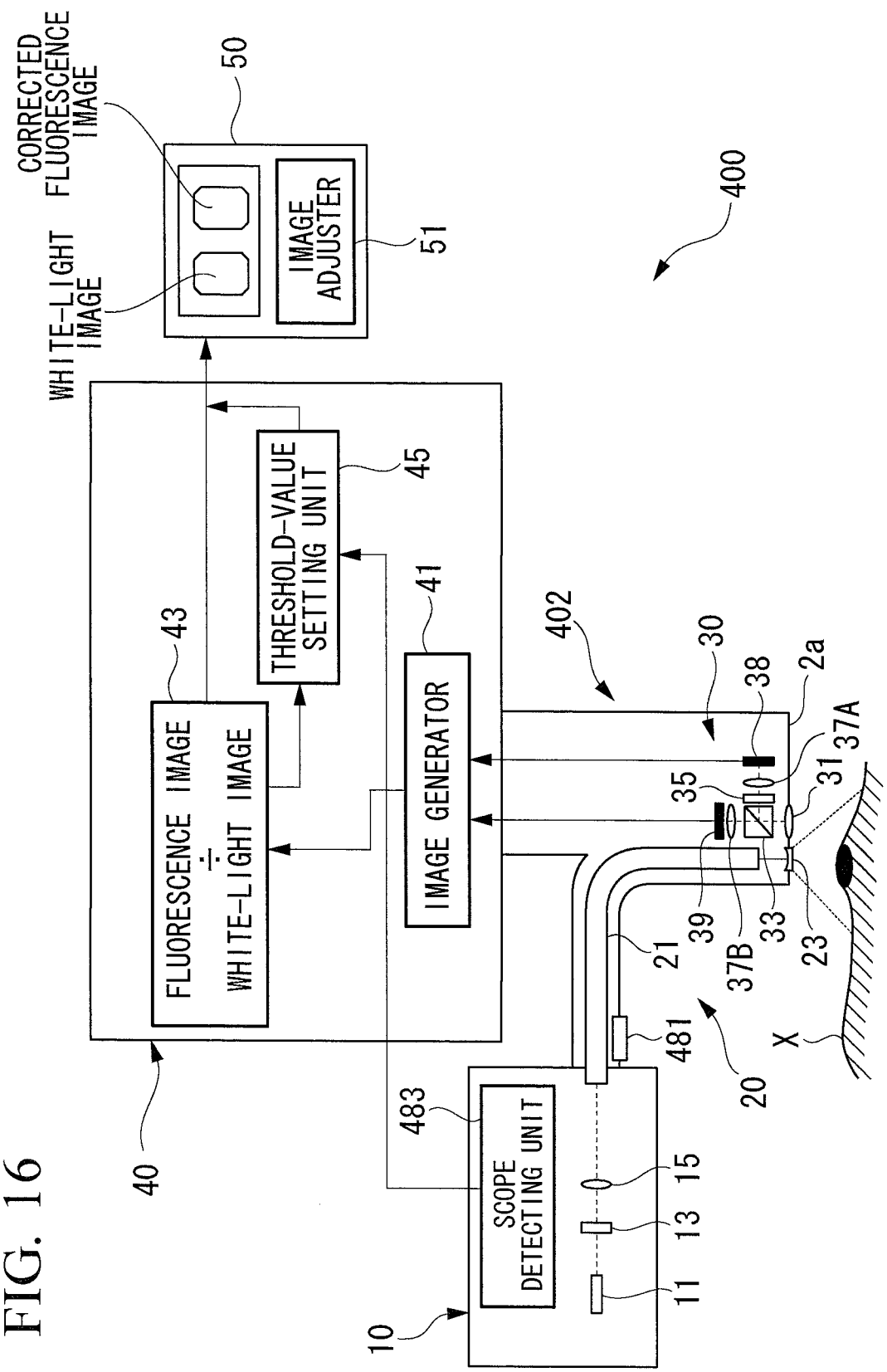
FIG. 16 schematically illustrates the configuration of a fluorescence endoscope device according to an eighth modification of the embodiment of the present invention.

Referring to FIG. 16, in an eighth modification, a fluorescence endoscope device 400 may include a detachable scope 402 having an IC chip 481 that stores scope information, and the light source 10 may include a scope detecting unit 483 that detects the scope information stored in the IC chip 481. The scope information includes the number of irradiating sections constituted by the light guide fiber 21 and the light spreading lens 23, an observation angle between the irradiating sections and a light receiving section constituted by the objective lens 31, and the like.

In this case, when the scope 402 is connected to the light source 10, the scope detecting unit 483 may read the scope information stored in the IC chip 481 and send the scope information to the threshold-value setting unit 45. Based on the scope information, the coefficients a and b may be selected. Because the observation magnification and the like vary depending on the type of the scope 402, the total number $n_1$ of pixels of the background and the total number $n_2$ of pixels of the lesion vary even if the same lesion is observed. Accordingly, threshold values corresponding to various types of scopes with different specifications and purposes can be set. In this case, the coefficients a and b may similarly be preset by using the aforementioned Tables 1 to 3.

Referring to FIG. 17, in a ninth modification, an image combiner 591 that generates a combined image constituted of a white-light image and a corrected fluorescence image may be provided, and the generated combined image may be displayed on a monitor 550.

Accordingly, the positional relationship between the white-light image and the corrected fluorescence image can be provided to an operator more clearly. Since an area lower than or equal to a threshold value is displayed as a gradation value of zero, the display of the white-light image is prevented from being hindered by the corrected fluorescence image in areas other than the lesion even in the combined image constituted of the superposed images.

Although the white-light image is used as a reference image in this modification, the white-light image may be acquired by using, for example, a CMOS device or a CCD (white-light-image acquisition unit) formed of three channels, i.e., R, G, and B channels, and the R channel alone, for example, may be used as the reference image.

Alternatively, light in a wavelength range different from that of white light, e.g., infrared or near-infrared light, may be radiated as additional reference light, so as to acquire a reference image different from the white-light image.

Although the embodiment of the present invention has been described above in detail with reference to the drawings, the specific configurations are not limited to those in the above embodiment and may include other design modifications so long as they do not depart from the scope of the invention. For example, the present invention is not limited to the above embodiment and the modifications thereof, and may be applied to an embodiment with an appropriate combination of the embodiment and the modifications thereof; the invention is not limited in particular.

Furthermore, in the above embodiment and the modifications thereof, although the image adjuster 51 eliminates the display of the fluorescence from the background and maintains the display of the lesion, for example, the gradation values of the pixels of the background may be reduced to an extent that the display of the background is not eliminated, and the gradation values of the pixels displaying the lesion may be increased, so long as the contrast between the fluorescence from the lesion and the fluorescence from the background can be increased.

REFERENCE SIGNS LIST 10 light source
41 image generator (fluorescence-image acquisition unit, reference-image acquisition unit)
43 image corrector (corrected-fluorescence-image generator)
45 threshold-value setting unit
50 monitor (display)
51 image adjuster
100 fluorescence endoscope device

The invention claimed is:
1. A fluorescence endoscope device comprising:
a light source that irradiates a subject with excitation light and reference light;
a fluorescence-image acquisition unit that acquires a fluorescence image by capturing fluorescence generated in the subject irradiated with the excitation light from the light source;
a reference-image acquisition unit that acquires a reference image by capturing return light returning from the subject irradiated with the reference light from the light source;
a corrected-fluorescence-image generator that corrects the fluorescence image acquired by the fluorescence-image acquisition unit by using the reference image acquired by the reference-image acquisition unit so as to generate a corrected fluorescence image;

a threshold-value setting unit that sets a threshold value on the basis of an average value of gradation values of pixels in the corrected fluorescence image generated by the corrected-fluorescence-image generator;

an image adjuster that increases the contrast in the corrected fluorescence image between an area having gradation values larger than the threshold value set by the threshold-value setting unit and an area having gradation values smaller than the threshold value; and a display unit that displays the corrected fluorescence image whose contrast is increased by the image adjuster.

2. The fluorescence endoscope device according to claim 1, wherein the reference-image acquisition unit acquires reflected light or spread light of the reference light returning after being reflected or spread at the subject.

3. The fluorescence endoscope device according to claim 1, wherein the light source further emits white light, the image adjuster generates an eliminated-background image in which the area having gradation values smaller than the threshold value is not displayed, the fluorescence endoscope device further comprises a white-light-image acquisition unit that acquires a white-light image of the subject irradiated with the white light; and an image combiner that generates a combined image by superposing the white-light image acquired by the white-light-image acquisition unit and the eliminated-background image generated by the image adjuster, and the display unit displays the combined image generated by the image combiner.

4. The fluorescence endoscope device according to claim 1, wherein the light source emits white light as the reference light, the reference-image acquisition unit acquires an image of the white light returning from the subject as the reference image, the image adjuster generates an eliminated-background image in which the area having gradation values smaller than the threshold value is not displayed, the fluorescence endoscope device further comprises an image combiner that generates a combined image by superposing the white-light image of the subject acquired by the reference-image acquisition unit and the eliminated-background image generated by the image adjuster, and the display unit displays the combined image generated by the image combiner.

5. The fluorescence endoscope device according to claim 1, wherein the corrected-fluorescence-image generator divides the fluorescence image by the reference image.

6. The fluorescence endoscope device according to claim 5, wherein the threshold-value setting unit sets a value obtained by multiplying a coefficient by the average value of the gradation values as the threshold value, the coefficient being set such that the coefficient decreases when a percentage at which an area with a predetermined gradation value or higher occupies the corrected fluorescence image increases.

7. The fluorescence endoscope device according to claim 5, wherein the threshold-value setting unit sets the threshold value on the basis of the average value of the gradation values and a standard deviation.

8. The fluorescence endoscope device according to claim 7, wherein the threshold-value setting unit sets a value obtained by adding the standard deviation to the average value of the gradation values as the threshold value.

9. The fluorescence endoscope device according to claim 7, wherein the threshold-value setting unit sets a value obtained by adding the standard deviation to a value obtained by multiplying a coefficient by the average value of the gradation values as the threshold value, the coefficient being set such that the coefficient decreases when a percentage at which an area with a predetermined gradation value or higher occupies the corrected fluorescence image increases.

10. The fluorescence endoscope device according to claim 7, wherein the threshold-value setting unit sets a value obtained by adding the average value of the gradation values to a value obtained by multiplying a coefficient by the standard deviation as the threshold value, the coefficient being set such that the coefficient decreases when a percentage at which an area with a predetermined gradation value or higher occupies the corrected fluorescence image increases.

11. The fluorescence endoscope device according to claim 7, wherein the threshold-value setting unit sets a value obtained by adding a first value to a second value as the threshold value, the first value being obtained by multiplying a first coefficient by the average value of the gradation values, the first coefficient being set such that the first coefficient decreases when a percentage at which an area with a predetermined gradation value or higher occupies the corrected fluorescence image increases, the second value being obtained by multiplying a second coefficient by the standard deviation, the second coefficient being set such that the second coefficient decreases when a percentage at which an area with a predetermined gradation value or higher occupies the corrected fluorescence image increases.

12. The fluorescence endoscope device according to claim 1, wherein the threshold-value setting unit sets a value obtained by multiplying a coefficient by the average value of the gradation values as the threshold value, the coefficient being set such that the coefficient decreases when a percentage at which an area with a predetermined gradation value or higher occupies the corrected fluorescence image increases.

13. The fluorescence endoscope device according to claim 1, wherein the threshold-value setting unit sets the threshold value on the basis of the average value of the gradation values and a standard deviation.

14. The fluorescence endoscope device according to claim 13, wherein the threshold-value setting unit sets a value obtained by adding the standard deviation to the average value of the gradation values as the threshold value.

15. The fluorescence endoscope device according to claim 13, wherein the threshold-value setting unit sets a value obtained by adding the standard deviation to a value obtained by multiplying a coefficient by the average value of the gradation values as the threshold value, the coefficient being set such that the coefficient decreases when a percentage at which an area with a predetermined gradation value or higher occupies the corrected fluorescence image increases.

16. The fluorescence endoscope device according to claim 13, wherein the threshold-value setting unit sets a value obtained by adding the average value of the gradation values to a value obtained by multiplying a coefficient by the standard deviation as the threshold value, the coefficient being set such that the coefficient decreases when a percentage at which an area with a predetermined gradation value or higher occupies the corrected fluorescence image increases.

17. The fluorescence endoscope device according to claim 13, wherein the threshold-value setting unit sets a value obtained by adding a first value to a second value as the threshold value, the first value being obtained by multiplying a first coefficient by the average value of the gradation values, the first coefficient being set such that the first coefficient decreases when a percentage at which an area with a predetermined gradation value or higher occupies the corrected fluorescence image increases, the second value being obtained by multiplying a second coefficient by the standard deviation, the second coefficient being set such that the second coefficient decreases when a percentage at which an area with a predetermined gradation value or higher occupies the corrected fluorescence image increases.

* * * * *